(12) United States Patent
Giachelli et al.

(10) Patent No.: US 6,551,990 B2
(45) Date of Patent: *Apr. 22, 2003

(54) METHODS OF INHIBITING ECTOPIC CALCIFICATION

(75) Inventors: Cecilia M. Giachelli, Mill Creek, WA (US); Susie Steitz, Seattle, WA (US)

(73) Assignee: University of Washington, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/206,576

(22) Filed: Dec. 7, 1998

(65) Prior Publication Data

US 2002/0032157 A1 Mar. 14, 2002

(51) Int. Cl.[7] ........................ A61K 38/16; A61K 38/17; A61K 38/18; A61K 38/19; A61K 38/22
(52) U.S. Cl. ............................ 514/2; 514/12; 424/85.1
(58) Field of Search ................................. 530/350, 824; 514/21, 2, 12; 424/85.1

(56) References Cited

U.S. PATENT DOCUMENTS

| | | | |
|---|---|---|---|
| 5,340,934 A | * | 8/1994 | Termine ............... 536/23.5 |
| 5,695,761 A | | 12/1997 | Denhardt et al. |
| 5,824,651 A | | 10/1998 | Nanci et al. |

FOREIGN PATENT DOCUMENTS

| | | |
|---|---|---|
| EP | 0 705 842 A2 | 4/1996 |
| WO | WO 92/22316 | 12/1992 |

OTHER PUBLICATIONS

Barisoni et al., "Osteopontin (OP) mRNA and Protein Expression in Glomerular Disease (GD) Correlates with Tubulo–Interstitial Damage (TID)" *J. Am. Soc. Nephrol* Abstract A2523, 7:1751 (1996).
Bautista et al., "A monoclonal antibody against Osteopontin inhibits RGD–mediated cell adhesion to osteopontin." *Annals New York Academy Sciences*, 760:309–311 (1995).
Bautista et al., "Low–Molecular–Weight Variants of Osteopontin Generated by Serine Proteinases in Urine of Patients With Kidney Stones" *J. of Cellular Biochemistry* 61:402–409 (1996).
Bautista et al., "Quantification of Osteopontin in Human Plasma With an ELISA: Basal Levels in Pre– and Post-menopausal Women" *Clincal Biochemistry* 29(3):231–239 (1996).
Boskey, Adele L., "Matrix Proteins and Mineralization: An Overview", *Connective Tissue Research*, 35(1–4):357–363 [411–417], (1996).

Boskey et al., "Osteopontin–hydroxyapatite interactions in vitro: inhibition of hydroxyapatite formation and growth in a gelatin–gel", *Bone and Mineral*, 22:147–159 (1993).
Butler et al., "Osteopontin", *Principles of Bone Biology*, 13:167–181 (1996).
Chen et al., "Calcium and Collagen Binding Properties of Osteopontin, Bone Sialoprotein, and Bone Acidic Glyco-protein–75 from Bone", *The Journal of Biological Chemistry*, 267(34):24871–24878 (1992).
Diamond et al., "Early and Persistent Up–Regulated Expression of Renal Cortical Osteopontin in Experimental Hydro-nephrosis", *Am. J. of Pathology* 146(6):1455–1466 (1995).
Fitzpatrick, et al., "Diffuse Calcification in Human Coronary Arteries", *The Journal of Clinical Investigation, Inc.*, 94:1597–1604 (1994).
Giachelli et al., "Osteopontin Is Elevated during Neointima Formation in Rat Arteries and Is a Novel Component of Human Atherosclerotic Plaques", *J. Clin. Invest.*, 92:1686–1696 (1993).
Giachelli et al., "Molecular and Cellular Biology of Osteopontin", *TCM*, 5(3):88–95 (1995).
Giachelli et al., "Osteopontin: Potential Roles in Vascular Function and Dystrophic Calcification", *J. Bone Miner Metab*, 15:179–183 (1997).
Hirota et al., "Expression of Osteopontin Messenger RNA by Macrophages in Atherosclerotic Plaques", *American Journal of Pathology*, 143(4):1003–1008 (1993).
Hunter et al., "Modulation of crystal formation by bone phosphoproteins: structural specificity of the osteopontin–mediated inhibition of hydroxyapatite formation", *Biochem. J.*, 300:723–728 (1994).
Ikeda et al., "Osteopontin mRNA Is Expressed by Smooth Muscle–derived Foam Cells in Human Atherosclerotic Lesions of the Aorta", *J. Clin. Invest.*, 92:2814–2820 (1993).
Khanna et al., "Captopril Prevents Increased Urinary and Renal Cortical Osteopontin in Stroke–Prone Spontaneously Hypertensive Rats" *J. Am. Soc. Nephrol.* Abstract A2452, 7:1737 (1996).
Kiefer et al., "The cDNA and derived amino acid sequence for human osteopontin", *Nucleic Acids Research*, 17(8) (1989).
Kim et al., "Dual Mechanisms for the Low Plasma Levels of Truncated Apolipoprotein B Proteins in Familial Hypobe-talipoproteinemia", *J. Clin. Invest.*, 101(6):1468–1477 (1998).
Kleinman et al., "Expression of osteopontin, a urinary inhibitor of stone mineral cyrstal growth, in rat kidney" *Kidney International* 47:1585–1596 (1995).

(List continued on next page.)

Primary Examiner—Elizabeth Kemmerer
(74) Attorney, Agent, or Firm—Campbell & Flores LLP

(57) ABSTRACT

The invention provides a method of inhibiting ectopic calcification in an individual. The method consists of administering to the individual a therapeutically effective amount of osteopontin or a functional fragment thereof.

8 Claims, 7 Drawing Sheets

OTHER PUBLICATIONS

Kleinman et al., "Upregulation of Osteopontin Expression by Ischemia in Rat Kidney" *Annals New York Academy of Sciences* 760:321–323 (1995).

Liang and Barnes, "Renal expression of osteopontin and alkaline phosphatase correlates with BUN levels in aged rats" *Am. J. Physiol.* 269:F398–F404 (1995).

Liaw et al., "Neutralizing Antibodies Directed Against Osteopontin Inhibit Rat Carotid Neointimal Thickening After Endothelial Denudation", *Arteriosclerosis, Thrmbosis, and Vascular Biology*, 17(1):188–193 (1997).

Liaw et al., "Osteopontin and $\beta_3$ Integrin Are Coordinately Expressed in Regenerating Endothelium In Vivo and Stimulate Arg–Gly–Asp–Dependent Endothelial Migration In Vitro", *Circulation Research*, 77(4):665–672 (1995).

Liaw et al., "Osteopontin Promotes Vascular Cell Adhesion and Spreading and IS Chemotactic for Smooth Muscle Cells In Vitro", *Circulation Research*, 74(2):214–224 (1994).

Liaw et al., "The Adhesive and Migratory Effects of Osteopontin Are Mediated via Distinct Cell Surface Integrins", *J. Clin. Invest.*, 95:713–724 (1995).

Liaw et al., "Altered Wound Healing in Mice Lacking a Functional Osteopontin Gene (sppl)", *J. Clin. Invest.*, 101(7):1468–1478 (1998).

Magil et al., "Osteopontin in chronic puromycin aminonucleoside nephrosis." *J. Amer. Society Nephrology*, 8:1383–1390 (1997).

McKee and Nanci, "Osteopontin at Mineralized Tissue Interfaces in Bone, Teeth, and Osseointegrated Implants: Ultrastructural Distritubion and Implications for Mineralized Tissue Formation, Turnover, and Repair", *Microscopy Research and Technique*, 33:141–164 (1996).

McKee and Nanci, "Secretion of Osteopontin by Macrophages and Its Accumulation at Tissue Surfaces During Wound Healing in Mineralized Tissues: A Potential Requirement for Macrophage Adhesion and Phagocytosis", *The Anatomical Record*, 245:394–409 (1996).

McKee and Nanci, "Osteopontin: An Interfacial Extracellular Matrix Protein in Mineralized Tissues." *Connective Tissue Research*, Vo.35(1–4):197–205[251–259] (1996).

O'Brien et al., "Osteopontin Is Expressed In Human Aortic Valvular Lesions", *Circulation*, vol. 92(8):2163–2168 (1995).

O'Brien et al., "Osteopontin Is Synthesized by Macrophage, Smooth Muscle,a nd Endothelial Cells in Promary and Restenotic Human Coronary Atherosclerotic Plaques", *Arterisclerosis and Thrombosis*, 14:1648–1656 (1994).

Pichler et al., "Pathogenesis of Cyclosporine Nephropathy: Roles of Angiotensin II and Osteopontin" *J. Am. Soc. Nephrol.* 6(4):1186–1196 (1995).

Ross et al., "Interactions between the Bone Matrix Proteins Osteopontin ad Bone Sialoprotein and the Osteoclast Integrin $\alpha_v\beta_3$ Potentiate Bone Resorption", *The Journal of Biological Chemistry*, 268:9901–9907 (1993).

Shen et al., "Ostepontin is Associated with Bioprostetic Heart Valve Calcification in Humans", *C.R. Acad. Sci.*, 320:49–57 (1997).

Shiraga et al., "Inhibition of calcium oxalate crystal growth in vitro by uropontin: Another member of the aspartic acid–rich protein superfamily", *Proc.Natl.Acad.Sci. USA*, 89:426–430 (1992).

Singh et al., "Calcium–Binding Properties of Osteopontin Derived from Non–Osteogenic Sources", *J. Biochem*, 114:702–707 (1993).

Sorenson and Petersen, "Identification of Two Phosphorylation Motifs in Bovine Osteopontin", *Biochemical and Biophysical Research Communications*, 198:200–205 (1994).

Sorensen et al., "Identification of a macromolecular crystal growth inhibitor in human urine as osteopontin" *Urol. Res.* 23:327–334 (1995).

Srivatsa et al., "Increased Cellular Expression of Matrix Proteins that Regulate Mineralization Is Associated with Calcification of Native Human and Porcine Xenograft Bioprosthetic Heart Valves", *The Journal of Clinical Investigation*, 99:996–1009 (1997).

Vyavahare et al., "Current Progress in Anticalcification for Bioprosthetic and Plymeric Heart Valves", *Cardiovascular Pathology*, 6(4):219–229 (1997).

Daoud et al., "Sequential Morphologic Studies of Regression of Advanced Atherosclerosis," *Arch. Pathol. Lab. Med.* 105:233–239 (1981).

Giachelli et al., "Evidence for a Role of Osteopontin in Macrophage Infiltration in Response to Pathological Stimuli in Vivo," *Amer. J. Pathology* 152(2):353–358 (1998).

Murry et al., "Macrophages Express Osteopontin During Repair of Myocardial Necrosis," *Amer. J. Pathology* 145(6):1450–1462 (1994).

* cited by examiner

```
      GACCAGACTC GTCCAGGCC AGTTGCAGCC TTCTCAGCCA AACGCCGACC AAGGAAAACT CACTACCATG AGAATTGCAG TGATTTGCTT TTGCCTCCTA
  101 GGCATCACCT GTGCCATACC AGTTAAACAG GCTGATTCTG AGCTTCTGA GGAAAAGCAG CTTTACACAA TGCTGTGGCC ACATGGCTAA
  201 ACCCTGACCC ATCTCAGAAG CAGAATCTCC TAGCCCCACA GAATGCTGTG GATGATGAAG CTTTAAACAA GAGACCCTTC CAAGTAAGTC
  301 CAACGAAAGC CATGACCACA TGGATGATAT GGATGATGAA CAGCCAGGAC TCCATGATGC TGAACGACTC CGAAGACTCA TGATGATGTA
  401 GATGACACTG ATGATTCTA CCAGTCTGAT GAGTCTCACC ATCTGATGAA TTTCCCAC GGACTGCCA GCAACCGAAG
  501 TTTTCACTCC AGTTGTCCCC ACAGTAGACA CATATGATGG CCGAGGTGAT AGTGTGGTT GTCAAAATCT AAGAGTTTC GCAGACCTGA
  601 CATCCAGTAC CCTGATGCTA CAGACGAGGA CATCACCTCA CACATGGAAA GCGAGGAGTT GAATGGTGCA TACAAGGCCA TCCCGGTTGC CCAGGACCTG
  701 AACGCGGCCT CTGATTGGGA CAGCCGTGGG AAGGACAGTT ATGAAACGAG TCAGCTGGAT GACCAGAGTG CTGAAACCCA CAGCCACAAG CAGTCCAGAT
  801 TATATAAGCG ATGCATTC CCAGTCTGAT GAGTCTCACC ATCTGATGAA GATGTGATT GATAGTCAGG ATAAACACT GAATTCCA GCCATGAATT
  901 TCACAGCCAT GAAGCCAT TGGTTGTAGA CCCCAAAGT TTCTCACTTT AAAGAAAA ATGCTTCTATG AATTAGATAG TGCATCTTCT
 1001 GAGGTCAATT AAAAGGAGAA AAAATACAAT TGTGTATCTA GCATTAGTC GAAATAACTA AGTGTTTGA AGAGAACATG AAATGCTTCT
 1101 TTCTCAGTTT ATTGTTGAA TGTGTATCTA GCATTAGTC GAAATAACTA AGAAATGCAA ACTATCACTG TATTTTAATA TTTGTTATTC TCTCATGAAT AGAAATTAT
 1201 ACTAAAAGCT TCAGGGTTAT GTCTATGTTC ATTCTATAGA AGAAATGCAA ACTATCACTG TATTTTAATA ATATAACTTT GTTTTTAAG TTAGTGTATA TTTGTTGTG
 1301 GTAGAAGCAA ACAAATACT TTTACCCACT TAAAAGAGA ATATAACATT TTATGTCACT TTATGTCACT ATAATCTTTT GTTTTTAAG TTAGTGTATA TTTGTTGTG
 1401 ATTATCTTTT TGTGGTGTGA ATAA
```

Fig. 1A

```
HUMAN   1  MRIAVICFCLLGITCAIPVKQADSGSSEEKQLYNKYPDAVATWLNPDPSQKQNLLAPQNAVSSEETNDFKQETLPSKSNESHDMDMDDEDD-DHVDS
      101  QDSIDSNDSDDVDDTDDSHQSDESHSDESDELVTDFPTDLPATEVFTPVVPTVDTYDGRGDSVVYGLRSKSKKFRRPDIQYPDATDEDITSHMESEELN
      201  GAYKAIPVAQDLNAPSDWDSRGKDSYETSQLDDQSAETHSHKQSRLYKRKANDESNEHSDV------------IDSQELSKVSREFHSHEFHSH
      301  EDMLVVDPKSKEEDKHLKFRISHELDSASSEVN
```

Fig. 1B

SEQUENCE LISTING

<160> NUMBER OF SEQ ID NOS: 10

<210> SEQ ID NO 1
<211> LENGTH: 1424
<212> TYPE: DNA
<213> ORGANISM: Homo sapiens
<220> FEATURE:
<221> NAME/KEY: CDS
<222> LOCATION: (68)..(1009)

<400> SEQUENCE: 1

```
gaccagactc gtctcaggcc agttgcagcc ttctcagcca aacgccgacc aaggaaaact      60 cactacc atg aga att gca gtg att tgc ttt tgc ctc cta ggc atc acc     109
        Met Arg Ile Ala Val Ile Cys Phe Cys Leu Leu Gly Ile Thr
            1               5                  10 tgt gcc ata cca gtt aaa cag gct gat tct gga agt tct gag gaa aag     157
Cys Ala Ile Pro Val Lys Gln Ala Asp Ser Gly Ser Ser Glu Glu Lys
 15                  20                  25                  30 cag ctt tac aac aaa tac cca gat gct gtg gcc aca tgg cta aac cct     205
Gln Leu Tyr Asn Lys Tyr Pro Asp Ala Val Ala Thr Trp Leu Asn Pro
                 35                  40                  45 gac cca tct cag aag cag aat ctc cta gcc cca cag aat gct gtg tcc     253
Asp Pro Ser Gln Lys Gln Asn Leu Leu Ala Pro Gln Asn Ala Val Ser
             50                  55                  60 tct gaa gaa acc aat gac ttt aaa caa gag acc ctt cca agt aag tcc     301
```

```
Ser Glu Glu Thr Asn Asp Phe Lys Gln Glu Thr Leu Pro Ser Lys Ser
        65                  70                  75 aac gaa agc cat gac cac atg gat gat atg gat gat gaa gat gat         349
Asn Glu Ser His Asp His Met Asp Asp Met Asp Asp Glu Asp Asp
    80                  85                  90 gac cat gtg gac agc cag gac tcc att gac tcg aac gac tct gat gat     397
Asp His Val Asp Ser Gln Asp Ser Ile Asp Ser Asn Asp Ser Asp Asp
 95                 100                 105                 110 gta gat gac act gat gat tct cac cag tct gat gag tct cac cat tct     445
Val Asp Asp Thr Asp Asp Ser His Gln Ser Asp Glu Ser His His Ser
            115                 120                 125 gat gaa tct gat gaa ctg gtc act gat ttt ccc acg gac ctg cca gca     493
Asp Glu Ser Asp Glu Leu Val Thr Asp Phe Pro Thr Asp Leu Pro Ala
        130                 135                 140 acc gaa gtt ttc act cca gtt gtc ccc aca gta gac aca tat gat ggc     541
Thr Glu Val Phe Thr Pro Val Val Pro Thr Val Asp Thr Tyr Asp Gly
    145                 150                 155 cga ggt gat agt gtg gtt tat gga ctg agg tca aaa tct aag aag ttt     589
Arg Gly Asp Ser Val Val Tyr Gly Leu Arg Ser Lys Ser Lys Lys Phe
160                 165                 170 cgc aga cct gac atc cag tac cct gat gct aca gac gag gac atc acc     637
Arg Arg Pro Asp Ile Gln Tyr Pro Asp Ala Thr Asp Glu Asp Ile Thr
175                 180                 185                 190 tca cac atg gaa agc gag gag ttg aat ggt gca tac aag gcc atc ccc     685
Ser His Met Glu Ser Glu Glu Leu Asn Gly Ala Tyr Lys Ala Ile Pro
                195                 200                 205 gtt gcc cag gac ctg aac gcg cct tct gat tgg gac agc cgt ggg aag     733
Val Ala Gln Asp Leu Asn Ala Pro Ser Asp Trp Asp Ser Arg Gly Lys
            210                 215                 220 gac agt tat gaa acg agt cag ctg gat gac cag agt gct gaa acc cac     781
Asp Ser Tyr Glu Thr Ser Gln Leu Asp Asp Gln Ser Ala Glu Thr His
        225                 230                 235 agc cac aag cag tcc aga tta tat aag cgg aaa gcc aat gat gag agc     829
Ser His Lys Gln Ser Arg Leu Tyr Lys Arg Lys Ala Asn Asp Glu Ser
    240                 245                 250 aat gag cat tcc gat gtg att gat agt cag gaa ctt tcc aaa gtc agc     877
Asn Glu His Ser Asp Val Ile Asp Ser Gln Glu Leu Ser Lys Val Ser
255                 260                 265                 270 cgt gaa ttc cac agc cat gaa ttt cac agc cat gaa gat atg ctg gtt     925
Arg Glu Phe His Ser His Glu Phe His Ser His Glu Asp Met Leu Val
                275                 280                 285 gta gac ccc aaa agt aag gaa gaa gat aaa cac ctg aaa ttt cgt att     973
Val Asp Pro Lys Ser Lys Glu Glu Asp Lys His Leu Lys Phe Arg Ile
            290                 295                 300 tct cat gaa tta gat agt gca tct tct gag gtc aat taaaaggaga         1019
Ser His Glu Leu Asp Ser Ala Ser Ser Glu Val Asn
        305                 310 aaaaatacaa tttctcactt tgcatttagt caaaagaaaa aatgctttat agcaaaatga  1079
aagagaacat gaaatgcttc tttctcagtt tattggttga atgtgtatct atttgagtct  1139
ggaaataact aatgtgtttg ataattagtt tagtttgtgg cttcatggaa actccctgta  1199
aactaaaagc ttcagggtta tgtctatgtt cattctatag aagaaatgca aactatcact  1259 gtatttttaat atttgttatt ctctcatgaa tagaaattta tgtagaagca aacaaaatac  1319
ttttacccac ttaaaagag aatataacat tttatgtcac tataatcttt tgttttttaa  1379
gttagtgtat attttgttgt gattatcttt ttgtggtgtg aataa                 1424

<210> SEQ ID NO 2
```

```
<211> LENGTH: 314
<212> TYPE: PRT
<213> ORGANISM: Homo sapiens

<400> SEQUENCE: 2

Met Arg Ile Ala Val Ile Cys Phe Cys Leu Leu Gly Ile Thr Cys Ala
 1               5                  10                  15

Ile Pro Val Lys Gln Ala Asp Ser Gly Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
            85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 3
<211> LENGTH: 10
<212> TYPE: PRT
<213> ORGANISM: Homo sapiens

<400> SEQUENCE: 3

Asp Asp Met Asp Asp Glu Asp Asp Asp
 1               5                  10

<210> SEQ ID NO 4
```

```
<211> LENGTH: 12
<212> TYPE: PRT
<213> ORGANISM: Homo sapiens

<400> SEQUENCE: 4

Asp Trp Asp Ser Arg Gly Lys Asp Ser Tyr Glu Thr
 1               5                  10

<210> SEQ ID NO 5
<211> LENGTH: 7
<212> TYPE: PRT
<213> ORGANISM: Homo sapiens

<400> SEQUENCE: 5

Ser Gly Ser Ser Glu Glu Lys
 1               5

<210> SEQ ID NO 6
<211> LENGTH: 24
<212> TYPE: PRT
<213> ORGANISM: Homo sapiens

<400> SEQUENCE: 6

Ser Lys Glu Glu Asp Lys His Leu Lys Phe Arg Ile Ser His Glu Leu
 1               5                  10                  15

Asp Ser Ala Ser Ser Glu Val Asn
            20

<210> SEQ ID NO 7
<211> LENGTH: 14
<212> TYPE: PRT
<213> ORGANISM: Homo sapiens

<400> SEQUENCE: 7

Asn Ala Val Ser Ser Glu Glu Thr Asn Asp Phe Lys Gln Glu
 1               5                  10

<210> SEQ ID NO 8
<211> LENGTH: 12
<212> TYPE: PRT
<213> ORGANISM: Homo sapiens

<400> SEQUENCE: 8

Ser Asp Glu Ser His His Ser Asp Glu Ser Asp Glu
 1               5                  10

<210> SEQ ID NO 9
<211> LENGTH: 10
<212> TYPE: PRT
<213> ORGANISM: Homo sapiens

<400> SEQUENCE: 9

Asp Gly Arg Gly Asp Ser Val Ala Tyr Gly
 1               5                  10

<210> SEQ ID NO 10
<211> LENGTH: 10
<212> TYPE: PRT
<213> ORGANISM: Homo sapiens

<400> SEQUENCE: 10

Arg Lys Lys Arg Ser Lys Lys Phe Arg Arg
 1               5                  10
```

METHODS OF INHIBITING ECTOPIC CALCIFICATION

This invention was made with government support under grant numbers HL40079-6A2 and HL18645 awarded by the National Institutes of Health and grant number EEC9520161 awarded by the National Science Foundation. The United States Government has certain rights in this invention.

BACKGROUND OF THE INVENTION

1. Field of the Invention

This invention relates generally to the field of medicine and, more specifically, to methods of inhibiting ectopic calcification.

2. Background Information

Deposition of calcium crystals in tissues other than teeth or bone, referred to as ectopic calcification, commonly occurs in association with renal failure, cardiovascular disease, diabetes and the aging process. A frequent finding in patients with renal failure, particularly those undergoing long-term hemodialysis and unable to appropriately regulate serum mineral balance, is calcification of internal organs, including the lung, heart, stomach and kidneys. Less commonly, hemodialysis patients develop painful calcified skin lesions that progress to non-healing ulcers or gangrene and may require amputation of the affected limb.

Ectopic calcification is also a common complication of the implantation of bioprosthetic heart valves and is the leading cause of replacement valve failure. Ectopic calcification also occurs in native heart valves and blood vessels in association with atherosclerosis, diabetes and cardiovascular disease. The deposition of minerals in the vasculature narrows the orifices and hardens the walls of the affected valves and blood vessels, resulting in reduced blood flow to the heart and peripheral organs. Therefore, ectopic calcification increases the risk of valve failure, stroke, ischemia and myocardial infarction.

One protein that is abundant at the sites of ectopic calcification, such as in atherosclerotic plaques and in calcified aortic valves, is osteopontin. Osteopontin has several known functions, including promoting cell adhesion, spreading and migration. Osteopontin colocalizes with sites of early calcification in coronary atherosclerotic plaques and its expression increases as atherosclerosis develops. These findings, combined with studies showing that osteopontin has calcium-binding properties in vitro, have led to the suggestion that osteopontin may be involved in ectopic calcification. Previous studies have not addressed the role of osteopontin in ectopic calcification in vivo.

Ectopic calcification, if left untreated, results in increased morbidity and death. Current therapies to normalize serum mineral levels or to inhibit calcification of vascular tissues or implants are of limited efficacy and cause unacceptable side effects.

Thus, there exists a need for an effective method of inhibiting ectopic calcification. The present invention satisfies this need and provides related advantages as well.

SUMMARY OF THE INVENTION

The invention provides a method of inhibiting ectopic calcification in an individual. The method consists of administering to the individual a therapeutically effective amount of osteopontin or a functional fragment thereof. The method can be used to inhibit ectopic calcification associated with a variety of conditions such as atherosclerosis, stenosis, restenosis, prosthetic valve replacement, angioplasty, renal failure, tissue injury, diabetes and aging.

BRIEF DESCRIPTION OF THE DRAWINGS

FIGS. 1a) and b) shows the nucleotide (SEQ ID NO:1) and amino acid sequence (SEQ ID NO:2) of human osteopontin, as described by Kiefer et al., *Nucleic Acids Res.* 17:3306 (1989).

DETAILED DESCRIPTION OF THE INVENTION

Figure 2A:
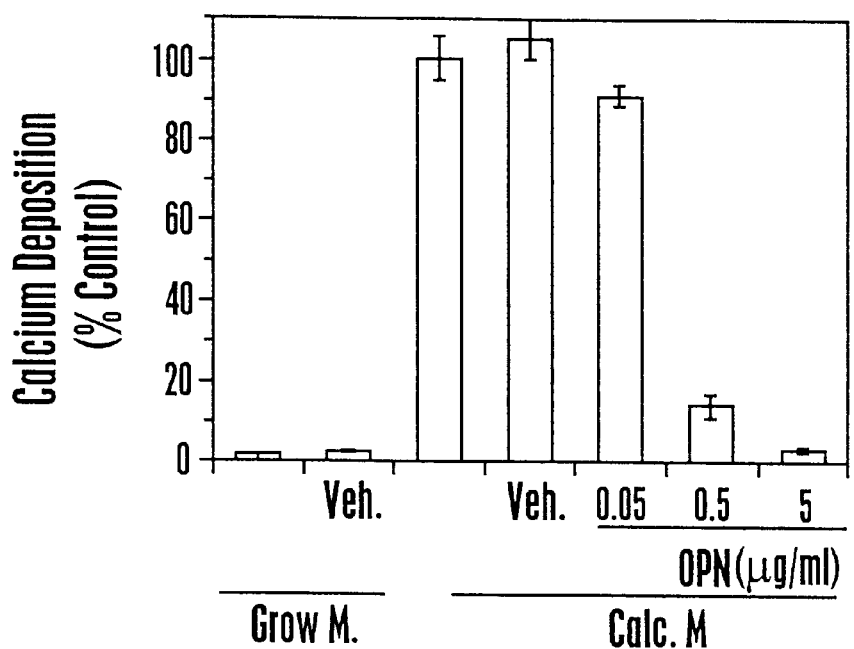
FIG. 2 shows the effects of osteopontin (a) on calcification of BASMC as compared to vitronectin and fibronectin (b).

The invention is directed to an effective method for the inhibition of ectopic calcification. Ectopic calcification commonly occurs in association with renal failure, cardiovascular disease, diabetes and the aging process. Ectopic calcification of the vasculature increases an individual's risk of myocardial infarction, ischemia, stroke, dissection after angioplasty and heart valve failure. Ectopic calcification of prosthetic implants, such as bioprosthetic heart valves, is the leading cause of implant failure. Therefore, the method will reduce disease and death associated with ectopic calcification.

The method is based on the discovery that osteopontin is able to effectively and specifically inhibit ectopic calcification. Therefore, ectopic calcification can be prevented or treated by administering a therapeutically effective amount of osteopontin or a functional fragment thereof to an individual, either systemically or at the predicted or known sites of ectopic calcification. As osteopontin is normally found in calcified tissues and at the sites of ectopic calcification, it can be administered with minimal toxic or immunogenic side effects.

As used herein, the term "ectopic calcification" is intended to mean the abnormal deposition of calcium crystals at sites other than bones and teeth. Ectopic calcification results in the accumulation of macroscopic hydroxyapatite deposits in the extracellular matrix.

Ectopic calcification can occur in a variety of tissues and organs and is associated with a number of clinical conditions. For example, ectopic calcification can be a consequence of inflammation or damage to the affected tissues or can result from a systemic mineral imbalance. Commonly, ectopic calcification occurs in vascular tissue, including arteries, veins, capillaries, valves and sinuses. Inflammation or damage to the blood vessels can occur, for example, as a result of environmental factors such as smoking and high-fat diet. Inflammation or damage can also occur as a result of trauma to the vessels that results from injury, vascular surgery, heart surgery or angioplasty. Vascular calcification is also associated with aging and with disease, including hypertension, atherosclerosis, diabetes, renal failure and subsequent dialysis, stenosis and restenosis.

Ectopic calcification also occurs in non-vascular tissues, such as tendons (Riley et al., Ann. Rheum. Dis. 55:109–115 (1996)), skin (Evans et al., *Pediatric Dermatology* 12:307–310 (1997)), sclera (Daicker et al., *Opthalmologica* 210:223–228 (1996) and myometrium (McCluggage et al., *Int. J. Gynecol. Pathol.* 15:82–84 (1996)), each of which is incorporated herein by reference. In diseases resulting in systemic mineral imbalance, such as renal failure and diabetes, ectopic calcification in visceral organs, including the lung, heart, kidney and stomach, is common (Hsu, *Amer. J. Kidney Disease* 4:641–649 (1997), incorporated herein by reference). Furthermore, ectopic calcification is a frequent complication of the implantation of biomaterials, prostheses and medical devices, including, for example, bioprosthetic heart valves (Vyavahare et al., *Cardiovascular Pathology* 6:219–229 (1997), incorporated herein by reference). The methods of the invention are applicable to ectopic calcification that occurs in association with all of these conditions.

The term "ectopic calcification" is not intended to refer to the calcification that normally occurs within the bone matrix during bone formation and growth. Ectopic calcification, as used herein, is also distinct from abnormal calcification that occurs in renal tubules and urine that results in the formation of primarily calcium oxalate-containing kidney stones.

As used herein, the term "inhibiting," in connection with inhibiting ectopic calcification, is intended to mean preventing, retarding, or reversing formation, growth or deposition of extracellular matrix hydroxyapatite crystal deposits.

As used herein, the term "osteopontin" is intended to mean a molecule that is able to inhibit ectopic calcification and that is recognizably similar to one or more molecules known in the art as osteopontin. Osteopontin is characterized as a phosphorylated sialoprotein having a predicted molecular weight of about 34 kDa. Due to high negativity, post-translational modifications and alternatively spliced isoforms, osteopontin has been reported to have an apparent molecular weight of between about 44 and 85 kDa as determined by sodium dodecyl sulfate-polyacrylamide gel electrophoresis (SDS-PAGE) (Giachelli et al., *Trends Cardiovasc. Med* 5:88–95 (1995)). All of the post-translationally modified forms and alternatively spliced isoforms of osteopontin are included within the definition of osteopontin as used herein.

Osteopontin has been identified in various species, including rat (Oldbert et al., *Proc. Natl., Acad. Sci. USA* 83:8819–8823 (1986)); mouse (Craig et al., *J. Biol. Chem.* 264:9682–9689(1989)); human (Kiefer et al., *Nucleic Acids Res.* 17:3306 (1989) and Young et al. *Genomics* 7:491–502 (1990)); pig (Wrana et al., *Nucleic Acids Res.* 17:10119 (1989)); cow (Kerr et al., *Gene* 108:237–243 (1991)); rabbit (Tezuka et al., *Biochem. Biophys. Res. Commun.* 186:911–917 (1992)); and chicken (Moore et al., *Biochemistry* 30:2502–2508 (1991)), each of which is incorporated herein by reference. Osteopontin from these species and osteopontin homologs from other vertebrates are included within the definition of osteopontin as used herein.

Osteopontin can be characterized by the presence of one or more domains that are conserved across known species. The conserved domains that characterize osteopontin include, for example, an N-terminal signal sequence, casein kinase II phosphorylation sites, an alternatively spliced domain, an Arg-Gly-Asp (RGD)-containing integrin-binding cell adhesion domain, an Asp-rich calcium binding domain, a calcium binding homology domain and two heparin binding homology domains (Giachelli et al., supra (1995)). Therefore, newly identified molecules that possess one or more of these characteristic features of osteopontin are also included within the definition of osteopontin.

Osteopontin is also known in the art as bone sialoprotein I, uropontin, secreted phosphoprotein I, 2ar, 2B7 and Eta 1 (Giachelli et al., supra (1995)). The molecules encompassed by all of these terms used in the art are included within the definition of osteopontin as used herein.

The nucleotide and deduced amino acid sequence for human osteopontin have been described by Kiefer et al., supra (1989), and are set forth herein as FIG. 1 (SEQ ID NOS:1 and 2). The term osteopontin is intended to include, for example, polypeptides having substantially the same amino acid sequence as shown as SEQ ID NO:2 and encoded by substantially the same nucleotide sequence as shown as SEQ ID NO:1.

Modifications of osteopontin and its functional fragments that either enhance or do not greatly affect the ability to inhibit ectopic calcification are also included within the term "osteopontin." Such modifications include, for example, additions, deletions or replacements of one or more amino acids from the native amino acid sequence of osteopontin with a structurally or chemically similar amino acid or amino acid analog. For example, the substitution of one or more phosphorylated amino acids, such as serine or threonine residues, by negatively charged amino acids, such as glutamic acid or aspartic acid, is contemplated. The substitution or addition of residues, such as kinase phosphorylation consensus sequences, that can be phosphorylated either in vivo or in vitro is also contemplated. Modifications of residues between the native sites of phosphorylation, such as to beneficially orient the phosphorylated residues to interact with hydroxyapatite or to reduce the distance between phosphorylation sites, is also contemplated. These modifications will either enhance or not significantly alter the structure, conformation or functional activity of the osteopontin or a functional fragment thereof.

Modifications that do not greatly affect the activity of osteopontin or its functional fragments can also include the addition or removal of sugar, phosphate or lipid groups as well as other chemical derivations known in the art. Additionally, osteopontin or its functional fragments can be modified by the addition of epitope tags or other sequences that aid in its purification and which do not greatly affect its activity.

As used herein, the term "functional fragment," in connection with osteopontin, is intended to mean a portion of osteopontin that maintains the ability of osteopontin to inhibit ectopic calcification. A functional fragment can be, for example, from about 6 to about 300 amino acids in length for example, from about 7 to about 150 amino acids in length, more preferably from about 8 to about 50 amino acids in length. If desired, a functional fragment can include regions of osteopontin with activities that beneficially cooperate with the ability to inhibit ectopic calcification. For example, a functional fragment of osteopontin can include sequences that promote the ingrowth of cells, such as endothelial cells and macrophages, at the site of ectopic calcification. Similarly, a functional fragment of osteopontin can include sequences, such as the RGD-containing domain, that beneficially promote cell adhesion and survival at the site of ectopic calcification.

As used herein, the term "individual" is intended to mean a human or other mammal, exhibiting, or at risk of developing, ectopic calcification. Such an individual can have, or be at risk of developing, for example, ectopic calcification associated with conditions such as atherosclerosis, stenosis, restenosis, renal failure, diabetes, prosthesis implantation, tissue injury or age-related vascular disease. The prognostic and clinical indications of these conditions are known in the art. An individual treated by a method of the invention can also be a candidate for, or have undergone, vascular surgery, including prosthetic valve replacement or angioplasty. An individual treated by a method of the invention can have a systemic mineral imbalance associated with, for example, diabetes, renal failure or kidney dialysis.

As used herein, the term "substantially the amino acid sequence," in reference to an osteopontin amino acid sequence or functional fragment thereof is intended to mean a sequence that is recognizably homologous to an osteopontin amino acid sequence and that inhibits ectopic calcification. For example, a sequence that is substantially the same as an osteopontin sequence can have greater than about 70% homology with an osteopontin sequence, preferably greater than about 80% homology, more preferably greater than about 90% homology.

As used herein, the term "prosthetic device" refers to a synthetic or biologically derived substitute for a diseased, defective or missing part of the body. As used herein, the term "bioprosthetic device" refers to a partially or completely biologically derived prosthetic device. Prosthetic devices are susceptible to ectopic calcification leading to premature failure, which can be inhibited by the methods of the invention. A prosthetic device can be implanted or attached at various sites of the body including, for example, the ear, eye, maxillofacial region, cranium, limbs and heart.

The methods of the invention can advantageously be used to prevent ectopic calcification of prosthetic heart valves, such as an aortic or atrioventricular valve, with or without a stent. Replacement heart valves can be made of a variety of materials, including metals, polymers and biological tissues, or any combination of these materials. Bioprosthetic valves include xenografted replacement valves from mammals, such as sheep, bovine and porcine, as well as human valves. Bioprosthetic heart valves are commonly subjected to tissue fixation and can additionally be devitalized prior to implantation.

The invention provides a method of inhibiting ectopic calcification in an individual. The method consists of administering to the individual a therapeutically effective amount of osteopontin or a functional fragment thereof. The method is advantageous as it employs a molecule that normally occurs at the site of ectopic calcification as a therapeutic agent. Therefore, the method will result in minimal toxicity, immunogenicity and side effects.

Osteopontin can be prepared or obtained by methods known in the art including, for example, purification from an appropriate biological source or by chemical synthesis. An appropriate biological source of osteopontin can be tissues, biological fluids or cultured cells that contain or express osteopontin. The presence and abundance of osteopontin protein in a particular source can be determined, for example, using ELISA analysis (Min et al., *Kidney Int.* 53:189–93 (1998), incorporated herein by reference) or immunocytochemistry (O'Brien et al., *Arterioscler. Thromb.* 14:1648–1656 (1994), incorporated herein by reference).

Osteopontin has been determined to be present in or expressed by kidney cells, hypertrophic chondrocytes, odontoblasts, bone cells, bone marrow, inner ear and brain cells. Osteopontin is also found in biological fluids, including milk and urine. Osteopontin is also present in tumors, particularly metastatic tumors and is a component of kidney stones (Butler et al., In: Principles of Bone Biology, Bilezikian et al., eds., Academic Press, San Diego, pp. 167–181 (1996), incorporated herein by reference). Osteopontin is also produced by smooth muscle cells, macrophages and endothelial cells at the site of vascular lesions (O'Brien et al., *Arterioscler. Thromb.* 14:1648–1656 (1994), incorporated herein by reference). Therefore, osteopontin can be purified from any of these sources using biochemical purification methods known in the art.

Osteopontin can also be obtained from the secreted medium of cells of any of the above tissue lineages grown in culture. For example, osteopontin can be substantially purified from the conditioned medium of smooth muscle cell cultures as described by Liaw et al., *Circ. Res.* 74:214–224 (1994), incorporated herein by reference.

The nucleotide sequences of osteopontin from a variety of species are known, as described previously. Therefore, osteopontin or its functional fragments can also be recombinantly expressed by appropriate host cells including, for example, bacterial, yeast, amphibian, avian and mammalian cells, using methods known in the art. Methods for recombinant expression and purification of peptides in various host organisms are described, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1989), both of which are incorporated herein by reference. Methods for the recombinant synthesis and purification of osteopontin and exemplary functional fragments therefrom are described, for example, in Smith et al., *J. Biol. Chem.* 271:28485–28491 (1996), incorporated herein by reference.

Following recombinant synthesis and purification, osteopontin and its functional fragments can be modified in a physiologically relevant manner by, for example, phosphorylation, acylation or glycosylation, using enzymatic methods known in the art. A kinase that can be used to phosphorylate osteopontin or its functional fragments at biologically relevant sites is casein kinase II, as described in Example IV. Other serine-threonine kinases known in the art, such as protein kinase C can also be used to phosphorylate osteopontin or its functional fragments.

The methods of the invention can be practiced using osteopontin or any of its functional fragments that possess the activity of inhibiting ectopic calcification. Fragments of osteopontin are selected, produced by methods known in the art and screened as described herein to determine their ability to inhibit ectopic calcification.

Fragments of osteopontin can be produced, for example, by enzymatic or chemical cleavage of osteopontin. Methods for enzymatic and chemical cleavage and for purification of the resultant protein fragments are well known in the art (see, for example, Deutscher, *Methods in Enzymology*, Vol.

182, "Guide to Protein Purification," San Diego: Academic Press, Inc. (1990), which is incorporated herein by reference). As an example, osteopontin contains a thrombin cleavage site between Arg169 and Ser170. Either the N-terminal cleavage fragment or the C-terminal cleavage fragment of osteopontin can be used in the methods of the invention.

Fragments of osteopontin can also be produced by chemical or recombinant synthesis of peptides that have substantially the sequence of osteopontin. For example, peptide libraries spanning overlapping sequences of osteopontin can be produced using methods known in the art and screened for their functional activity as described herein. Additionally, fragments corresponding to the N-terminal thrombin cleavage fragment or the C-terminal thrombin cleavage fragment of osteopontin can be recombinantly produced, as described by Smith et al., supra 271:28485–28491 (1996) and used in the methods of the invention.

As disclosed herein, osteopontin can inhibit ectopic calcification by directly adsorbing to and inhibiting apatite crystal growth and formation. Therefore, functional fragments of osteopontin can be selected based on their predicted ability to bind to calcium or calcium deposits. Regions that are contemplated to bind calcium include the aspartic acid rich sequence and the calcium binding homology domain. Therefore, a functional fragment of osteopontin can include, for example, substantially the sequence of the aspartic-rich calcium binding domain, DDMDDEDDDD (SEQ ID NO:3) or include substantially the sequence of the calcium binding homology domain, DWDSRGKDSYET (SEQ ID NO:4).

Additionally, as disclosed herein, phosphorylation can regulate the ability of osteopontin to inhibit ectopic calcification. Therefore, functional fragments of osteopontin can be selected by the presence of phosphorylation consensus sequences. A functional fragment of osteopontin can to chosen to include, for example, substantially the sequence of the casein kinase II phosphorylation consensus region, SGSSEEK (SEQ ID NO:5), or the C-terminal heparin binding homology domain SKEEDKHLKFRISHELDSASSEVN (SEQ ID NO:6), which contains three conserved sites of serine phosphorylation. A functional fragment of osteopontin can alternatively or additionally include the alternatively spliced domain, NAVSSEETNDFKQE (SEQ ID NO:7), which contains two sites of serine phosphorylation. Additional sites of serine and threonine phosphorylation are described, for example, by Sorensen et al., Bioc. Biophys. Res. Comm. 198:200–205 (1994), incorporated herein by reference. A functional fragment of osteopontin can include one or several of these phosphorylated residues together with flanking amino acids.

Fragments of osteopontin having the ability to inhibit ectopic activity include regions of the molecule that are highly conserved among species. Regions within human osteopontin with high sequence conservation are presented, for example, in Giachelli et al., supra (1995). For example, a functional fragment can include the highly conserved sequence SDESHHSDESDE (SEQ ID NO:8). A functional fragment of osteopontin can also include the conserved cell adhesion domain, DGRGDSVAYG (SEQ ID NO:9) or the heparin binding homology domain RKKRSKKFRR (SEQ ID NO:10).

If desired, such as to optimize their functional activity, selectivity, stability or bioavailability, osteopontin or a functional fragment thereof can be modified to include D-stereoisomers, non-naturally occurring amino acids, and amino acid analogs and mimetics. Examples of modified amino acids are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

If desired, one or more phosphorylated serine or threonine residues can be substituted by negatively charged amino acids, such as glutamic acid or aspartic acid. Such a modification can be advantageously made to reduce the susceptibility of osteopontin or a functional fragment to inactivation by phosphatases.

The ability of osteopontin or a fragment selected and prepared as described above to inhibit ectopic calcification can be assayed by a variety of in vitro and in vivo assays known in the art or described herein. For example, as described in Example I, cultured vascular cells, such as bovine aortic smooth muscle cells, form calcified deposits in a time-dependent manner when treated with calcification medium containing β-glycerophosphate. Additionally, as described in Example III, human vascular smooth muscle cells form calcified deposits in the presence of elevated levels of inorganic phosphate. Other culture systems for assaying the efficacy of osteopontin or a functional fragment thereof in inhibiting ectopic calcification can be determined by those skilled in the art. For example, osteopontin can be assayed using cells or tissues derived from other sites in the body where ectopic calcification occurs including, for example, viscera, skin, and endothelial cells.

The amount or extent of calcification prior to and following administering osteopontin or a functional fragment can be determined using such culture systems, either qualitatively by a visual or histochemical assessment, or by more quantitative methods. For example, calcified deposits can be detected visually as opaque areas by light microscopy and as black areas by von Kossa staining. The amount or extent of calcification can also be quantitatively assessed by the method described by Jono et al., *Arterioscler. Thromb. Vasc. Biol.* 17:1135–1142 (1997), incorporated herein by reference, or by using a commercially available colorimetric kit such as the Calcium Kit available from Sigma. Alternatively, the amount or extent of calcification can also be quantitatively assessed using known methods of atomic absorption spectroscopy.

As described in Examples I and III, the calcified deposits observed in cultured vascular smooth muscle cells, as assessed by histochemical, ultrastructural and electron diffraction analysis, can resemble the apatite deposits present at sites of ectopic calcification. Therefore, the ability of osteopontin or a functional fragment thereof to inhibit the deposition of calcium by cultured cells, in comparison with a vehicle or protein control, is an accurate indicator of its ability to inhibit ectopic calcification in an individual.

The ability of osteopontin or a functional fragment thereof to inhibit ectopic calcification can also be tested in animal models known in the art to be reliable indicators of the corresponding human pathology. For example, ectopic calcification can be induced by the subcutaneous or circulatory implantation of bioprosthetic valves, such as porcine, sheep or bovine valves, into animals as described, for example, in Vyavahare et al., supra (1997). A reduction in the amount or rate of valve calcification by administration of osteopontin or a functional fragment-can be detected, and is a measure of the functional activity of the preparation.

Similarly, animal models that are reliable indicators of human atherosclerosis, renal failure, hyperphosphatemia, diabetes, age-related vascular calcification and other conditions associated with ectopic calcification are known in the art. For example topical and systemic calciphylaxis, calcinosis and calcergy, which are experimental models of ectopic calcification are described, for example, in Bargmann, *J. Rheumatology* 22:5–6 (1995), Lian et al., *Calcified Tissue International*, 35:555–561 (1983) and Boivin et al., *Cell and Tissue Res.* 247:525–532 (1987). An experimental model of calcification of the vessel wall is described, for example, by Yamaguchi et al., *Exp. Path.* 25:185–190 (1984).

A preferred animal model for examining ectopic calcification and the effect of osteopontin preparations is an osteopontin-deficient mouse, described by Liaw et al., *J. Clin. Invest.* 101:1468–1478 (1998), incorporated herein by reference, in which, as described in Example V, ectopic calcification is enhanced compared to wild-type control animals.

Medical imaging techniques known in the art, such as magnetic resonance imaging, X-ray imaging, computed tomography and ultrasonography, can be used to assess the efficacy of osteopontin or a functional fragment thereof in inhibiting ectopic calcification in either a human or an animal. For example, the presence and extent of calcium deposits within vessels can be determined by the intravascular ultrasound imaging method described by Fitzgerald et al., *Circulation* 86:64–70 (1994), incorporated herein by reference. A decrease in the amount or extent of ectopic calcification can readily be identified and is indicative of the therapeutic efficacy of osteopontin or a functional fragment thereof.

Osteopontin or its functional fragments, assayed for their functional activity as described above, are administered to an individual in a therapeutically effective amount to inhibit ectopic calcification. Appropriate formulations, dosages and routes of delivery for administering osteopontin or a functional fragment are well known to those skilled in the art and can be determined for human patients, for example, from animal models as described previously. The dosage of osteopontin or a functional fragment thereof required to be therapeutically effective can depend, for example, on such factors as the extent of calcification, the site of calcification, the route and form of administration, the bio-active half-life of the molecule being administered, the weight and condition of the individual, and previous or concurrent therapies. The appropriate amount considered to be a therapeutically effective dose for a particular application of the method can be determined by those skilled in the art, using the guidance provided herein. One skilled in the art will recognize that the condition of the patient needs to be monitored throughout the course of therapy and that the amount of the composition that is administered can be adjusted accordingly.

For treating humans, a therapeutically effective amount of osteopontin or its functional fragments can be, for example, between about 10 µg/kg to 500 mg/kg body weight, for example, between about 0.1 mg/kg to 100 mg/kg, or between about 1 mg/kg to 50 mg/kg, depending on the treatment regimen. For example, if osteopontin or a functional fragment is administered several times a day, or once a day, or once every several days, a lower dose would be needed than if osteopontin or a functional fragment were administered only once, or once a week, or once every several weeks. Similarly, formulations that allow for timed-release of osteopontin would provide for the continuous release of a smaller amount of osteopontin than would be administered as a single bolus dose.

Osteopontin or a functional fragment can be delivered systemically, such as intravenously or intraarterially, to inhibit ectopic calcification throughout the body. Osteopontin or a functional fragment can also be administered locally at a site known to contain or predicted to develop ectopic calcification. Such a site can be, for example, an atherosclerotic plaque, a segment of artery undergoing angioplasty or the site of prosthetic implantation. Appropriate sites for administration of osteopontin and its functional fragments can be determined by those skilled in the art depending on the clinical indications of the individual being treated and whether or not the individual is concurrently undergoing invasive surgery.

Administration of osteopontin or a functional fragment can be achieved using various formulations of osteopontin. If desired, osteopontin can be administered as a solution or suspension together with a pharmaceutically acceptable carrier. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can additionally contain physiologically acceptable compounds that act, for example, to stabilize or increase the absorption of osteopontin or a functional fragment. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients. Osteopontin can also be formulated with a material such as a biodegradable polymer or a micropump that provides for controlled slow release of the molecule. Additionally, osteopontin can be formulated with a molecule, such as a phosphatase inhibitor, that reduces or inhibits dephosphorylation of osteopontin.

Osteopontin or a functional fragment can also be expressed from cells that have been genetically modified to express the protein. Expression of osteopontin from a genetically modified cell provides the advantage that sustained localized or systemic expression of the protein can occur, thus obviating the need for repeated administrations.

Methods for recombinantly expressing proteins in a variety of mammalian cells for therapeutic purposes are known in the art and are described, for example, in Lee et al., *Transfusion Medicine II* 9:91–113 (1995), which is incorporated herein by reference. Types of cells that are particularly amenable to genetic manipulation include, for example, hematopoietic stem cells, hepatocytes, vascular endothelial cells, keratinocytes; myoblasts, fibroblasts and lymphocytes.

A nucleic acid encoding osteopontin or a functional fragment can be operatively linked to a promoter sequence, which can provide constitutive or, if desired, inducible expression of appropriate levels of the encoded protein. Suitable promoter sequences for a particular application of the method can be determined by those skilled in the art and will depend, for example, on the cell type and the desired osteopontin expression level.

The nucleic acid encoding osteopontin or a functional fragment thereof can be inserted into a mammalian expression vector and introduced into cells by a variety of methods known in the art (see, for example, Sambrook et al., supra (1989); and Ausubel et al., supra (1994)). Such methods include, for example, transfection, lipofection, electroporation and infection with recombinant vectors. Infection with viral vectors such as retrovirus, adenovirus or adenovirus-associated vectors is particularly useful for genetically modifying a cell. A nucleic acid molecule also can be introduced into a cell using known methods that do not require the initial introduction of the nucleic acid sequence into a vector.

In one embodiment of the invention, a prosthetic device can be contacted with osteopontin or a functional fragment thereof. Contacting a prosthetic device with osteopontin or a functional fragment will effectively prevent or reduce ectopic calcification of the prosthetic device, preventing failure of the device and the need for premature replacement. The prosthetic device can be contacted with osteopontin or a functional fragment either prior to, during or following implantation into an individual, as needed.

Osteopontin or a functional fragment can contact a prosthetic device by attaching the molecule either covalently or non-covalently to the prosthetic device. An appropriate attachment method for a particular application of the method can be determined by those skilled in the art. Those skilled in the art know that an appropriate attachment method is compatible with implantation of the prosthetic device in humans and, accordingly, will not cause unacceptable toxicity or immunological rejection. Additionally, an appropriate attachment method will enhance or not significantly reduce the ability of osteopontin or a functional fragment thereof to inhibit ectopic calcification of the prosthetic device and the surrounding tissue.

Methods for covalently attaching proteins to polymers, metals and tissues are known in the art. For example, osteopontin can be attached to the prosthetic device using chemical cross-linking. Chemical cross-linking agents include, for example, glutaraldehyde and other aldehydes. Cross-linking agents that link osteopontin or a functional fragment thereof to a prosthetic device through either a reactive amino acid group, a carbohydrate moiety, or an added synthetic moiety are known in the art. Such agents and methods are described, for example, in Hermason, *Bioconjugate Techniques*, Academic Press, San Diego (1996), which is incorporated herein by reference. These methods can be used to contact a prosthetic device with a therapeutically effective amount of osteopontin or a functional fragment thereof.

Osteopontin can also be attached non-covalently to the prosthetic device by, for example, adsorption to the surface of the prosthetic device. A solution or suspension containing osteopontin or a functional fragment thereof, together with a pharmaceutically acceptable carrier, if desired, can be coated onto the prosthetic device in a therapeutically effective amount.

To provide sustained delivery of osteopontin or a functional fragment, a prosthetic device can also be contacted with osteopontin or a functional fragment thereof produced by cells attached to the prosthetic device. Such cells can be seeded onto the prosthetic device and expanded either ex vivo or in vivo. Appropriate cells include cells that normally produce and secrete osteopontin including, for example, macrophages, smooth muscle cells or endothelial cells. Additionally, cells that have been genetically modified to produce osteopontin or a functional fragment thereof including, for example, endothelial cells and fibroblasts, can be attached to the prosthetic device. The cells that are attached to the prosthetic device are preferably either derived from the individual receiving the prosthetic implant, or from an immunologically matched individual to reduce the likelihood of rejection of the implant.

The ability of osteopontin or a functional fragment that contacts a prosthetic device to inhibit ectopic calcification can be determined by various methods known in the art. One such method is to implant the prosthetic device into animals and measure calcium deposition, as described in Example V, in response to administration of osteopontin or a functional fragment thereof. Either a decrease in the rate or the amount of calcium deposition at the site of the explant is indicative of the therapeutic efficacy of the composition.

It is understood that modifications that do not substantially affect the activity of the various embodiments of this invention are also included within the definition of the invention provided herein. Accordingly, the following examples are intended to illustrate but not limit the present invention.

EXAMPLE I

Calcification of Cultured Bovine Vascular Cells

This example demonstrates that calcium deposition by cultured bovine aortic smooth muscle cells is a credible model of ectopic calcification. Methods for inducing physiologically relevant calcification are described. These methods can be used to assay preparations of osteopontin and fragments thereof for their ability to inhibit ectopic calcification.

Culture of Bovine Aortic Smooth Muscle Cells

BASMCs were obtained by a modification of the explant method originally described by Ross et al., *J. Cell Biol.*, 50:172–186 (1971), which is incorporated herein by reference. Briefly, medial tissue was separated from segments of bovine thoracic aorta. Small pieces of tissue (1 to 2 mm$^3$) were loosened by a one-hour incubation in DMEM containing 4.5 g/L of glucose supplemented with 165 U/ml collagenase type I, 15 U/ml elastase type III and 0.375 mg/mL soybean trypsin inhibitor at 37° C. Partially digested tissues were placed in 6-well plates and cultured for several weeks in DMEM containing 4.5 g/L of glucose supplemented with 20% FBS at 37° C. in a humidified atmosphere containing 5% $CO_2$. Cells that had migrated from the explants were collected and maintained in growth medium (DMEM containing 15% FBS and 10 mM sodium pyruvate supplemented with 100 U/ml of penicillin and 100 μg/ml of streptomycin). To confirm that the cells isolated from bovine aortic wall were vascular smooth muscle cells, α-smooth muscle actin, vimentin, and calponin levels were examined by immunofluorescence microscopy.

For immunofluorescence microscopy, BASMCS were cultured on 10-well heavy TEFLON synthetic fluorine-containing resin coated microscope glass slides (Cel-Line Associates Inc., USA) for 24 hours, fixed with cold methanol, blocked with PBS containing 2% BSA and 10% normal rabbit serum, and treated with monoclonal anti-α-smooth muscle actin antibody (1A4, Sigma) and monoclonal anti-vimentin antibody (V9, Dako) diluted with PBS containing 2% BSA 1:50 and 1:25, respectively. Monoclonal anti-calponin antibody (CALP), Frid et al., *Dev. Biol.*, 153:185–193 (1992), was used without dilution. As a secondary antibody, FITC-conjugated rabbit anti-mouse IgG was used after dilution with PBS 1:30. Mouse non-immune IgG was used as a control for the primary antibody.

Greater than 95% of the cells obtained as described above were stained with α-smooth muscle actin, vimentin, and calponin antibodies in a filamentous pattern, indicating that the cultured cells were of vascular smooth muscle origin. For all experiments, cells were used between passages 2 and 5.

Calcium Deposition By Bovine Aortic Smooth Muscle Cells

In order to examine calcification by cultured BASMC smooth muscle cells, calcification was induced by the method described by Shioi et al., *Arterioscler Thromb Vasc Biol.*, 15:2003–2009 (1995), which is incorporated herein by reference. Briefly, BASMC were cultured in growth medium for 4 days, and then switched to calcification medium (DMEM (high glucose, 4.5 g/L) containing 15% FBS and 10 mM sodium pyruvate in the presence of 10 mM of β-glycerophosphate (unless otherwise stated), $10^{-7}$ M insulin, and 50 μg/ml of ascorbic acid, supplemented with 100 U/ml of penicillin and 100 μg/ml of streptomycin) for 10 days. The medium was replaced with fresh medium twice a week. In the time course experiments, the beginning day of culture in calcification medium was defined as day 0.

Calcification was assessed by a modification of the method described by Jono et al., *Arterioscler. Thromb. Vasc. Biol.* 17:1135–1142 (1997) which is incorporated herein by reference. Briefly, the cultures were decalcified with 0.6 N HCl for 24 hours. The calcium content of the HCl supernatant was determined calorimetrically by the o- cresolphthalein complexone method (Calcium Kit, Sigma). After decalcification, the cultures were washed with phosphate-buffered saline (PBS) and solubilized with 0.1 N NaOH/O. 1% sodium dodecyl sulfate (SDS). Total protein content was measured with a BIO-RAD Protein Assay Kit (BIO-RAD). The calcium content of the cell layer was normalized to protein content. Phosphorus and calcium concentrations in the culture medium were measured by the phosphomolybdate complex method (Phosphorus Kit, Sigma) and the o-cresolphthalein complexone method (Calcium Kit, Sigma), respectively. Values were expressed as the mean +/- SEM, n=3.

BASMC treated with calcification medium containing β-glycerophosphate initiated calcium-containing mineral deposition in a time-dependent manner over the course of 14 days. In contrast, BASMC cultured in growth medium lacking β-glycerophosphate did not calcify. Addition of β-glycerophosphate resulted in an increased phosphorus concentration which correlated positively with calcium deposition in the cell layer. Conversely, calcium concentration decreased in the culture medium as the cell layer became calcified.

The effects of β-glycerophosphate on calcium deposition, phosphorus concentration and calcium concentration in the medium were dose-dependent. Calcium deposition depended on the initial concentration of β-glycerophosphate and was half-maximal at ~4 mM β-glycerophosphate. Phosphorus concentration in the culture medium increased with increasing concentrations of β-glycerophosphate over the range of 0 to 10 mM. Calcium deposition in the culture medium was inversely proportional to calcium deposition in the cell layer.

The observed calcification was not due to spontaneous precipitation of mineral from the media as supplementation of the culture media with up to 10 mM inorganic phosphate failed to form calcified deposits in the absence of cells. Nor did addition of-calcification media to endothelial cell cultures induce mineralization.

These results indicate that the calcification of BASMC under conditions which elevate inorganic phosphate in the media is a specific, cell- and matrix-mediated event.

Morphology of BASMC Calcification

To determine whether the calcification process in the BASMC cultures represented a physiologic-type of mineralization, histochemical, ultrastructural, and electron diffraction analyses were performed.

Mineral deposition by BASMC cultures was assessed histochemically by von Kossa staining (30 minutes, 5% silver nitrate) and light microscopy using the method described by Mallory, F. B., in Pathological Techniques, Second Edition, Philadelphia, W B Saunders Co., p. 152 (1942), which is incorporated herein by reference). The expression of alkalinephosphatasee was visualized by incubating citrate-acetone-formaldehyde fixed cells at room temperature for 15 minutes with Naphthol AS-BI Alkaline Solution (Sigma).

For ultrastructural examination by transmission electron microscopy (TEM), BASMC cells grown on plastic were fixed overnight in an aldehyde solution containing 1% glutaraldehyde and 1% paraformaldehyde buffered with 0.1 M sodium cacodylate buffer at pH 7.2. The cultures were then washed with 0.1 M sodium cacodylate buffer alone, dehydrated in a graded series of ethanol solutions, and infiltrated and embedded in either TAAB epoxy resin or LR WHITE acrylic resin (MARIVAC, Nova Scotia, Canada). The resins were polymerized for 2 days at 55° C. Samples destined for epoxy embedding were also post-fixed with potassium ferrocyanide-reduced 4% osmium tetroxide to provide additional membrane contrast in the electron microscope.

For mineral analyses by selected-area electron diffraction, other cultures were treated nonaqueously by fixing only with 100% ethanol, followed by direct embedding in resin without further processing. One micrometer-thick survey sections were prepared from various regions of the cultures and stained with Toluidine blue for examination by light microscopy. Thin sections (80–100 nm) of selected regions were then cut using a diamond knife on a Reichert ULTRACUT E microtome and placed on FORMVAR-coated nickel grids evaporated with carbon. Grid-mounted sections were stained briefly with ethanolic uranyl acetate and lead citrate and examined using a JEOL JEM 1200EX transmission electron microscope operating at 60 kV. Anhydrously treated samples left unstained were used for selected-area electron diffraction using a 100 μM diffraction aperture and a camera length of 80 cm. Diffraction patterns were analyzed and compared with synthetic apatite standards and powder diffraction files as previously reported for bone mineral (Landis et al., *J. Ultrastruc. Res.*, 63:188–223 (1978), incorporated herein by reference).

By light microscopy, BASMC cultures grown in growth medium showed areas of monolayer and multilayered growth typical for these types of cells. Following treatment with calcification medium for 10 days, the cultures showed extensive deposition of mineral, predominantly in multilayered areas. Von Kossa staining confirmed the presence of phosphate-containing mineral in these cultures. The calcification was most often observed in the extracellular matrix between cells, and was typically more pronounced at the basal aspect of the culture. The BASMCs in these calcified cultures were also positive for alkaline phosphatase activity.

At 14 days of culture (10 days with β-glycerophosphate), BASMC were monolayered or multilayered and at some locations formed nodules of cells. Ultrastructurally, where multilayered or nodular in appearance, the cells were associated with abundant extracellular matrix rich in collagen fibrils. At sites of this extracellular matrix accumulation, cells exhibited well-developed organelles typically associated with protein synthesis and secretion. A prominent cytoskeleton was evidenced by an extensive network of intracellular microfilaments, most likely composed of actin.

Whereas cells cultured without β-glycerophosphate showed no evidence of extracellular matrix calcification, those cultured with the added organic phosphate source showed several morphologically distinct forms of calcification associated with the cell layer. These included roughly spherical aggregates of calcified collagen fibrils, nodular deposits with increased mineral density at the periphery, and more diffuse calcification involving both the intra- and interfibrillar compartments of the extracellular matrix. At these latter sites, crystals having somewhat larger dimensions were observed to extend from one collagen fibril to another. Membrane-bounded matrix vesicles were also found in the extracellular matrix. Selected-area electron diffraction of anhydrously treated and unstained tissue sections of BASMC cultures containing calcified deposits identified the mineral phase as apatite, showing prominent diffraction reflections (from lattice planes 002, 211, 112, 300) whose indices were characteristic for this type of mineral.

Alkaline phosphatase is required for normal bone mineralization (Whyte et al. *Endocr. Rev.*, 15:439–461 (1994)) and has been shown to be required for calcification of osteoblast and cartilage cell cultures in response to β-glycerophosphate (Tenenbaum et al., *Bone Mineral*, 2:13–26 (1987)). To determine whether alkaline phosphatase was required for calcification in BASMCs under the conditions used in these studies, cultures were treated with the alkaline phosphatase inhibitor levamisole, or with vehicle alone. Calcium deposition in BASMC cultures was dose-dependently inhibited by levamisole. Half-maximal inhibition was observed at $5 \times 10^{-5}$ M levamisole. Vehicle treatment had no effect. Levamisole treatment was associated with a decrease in phosphorus concentration and maintenance of high calcium concentration in the culture medium.

These results indicate that calcification of the matrix deposited by BASMC cultures resembles the mineralization observed at sites of ectopic calcification in regard to mineral type (apatite) and the ultrastructure of the calcified deposits. For example, mineralization occurred predominantly in association with extracellular matrix collagen fibrils and matrix vesicles. Similar vesicular structures have been reported in calcified atherosclerotic plaques in association with elevated alkaline phosphatase activity (Kim et al., *Fed Proc*, 35:156–162 (1976)). Additionally, the nodular calcifications present in the calcifying BASMC cultures indicate spherulitic crystal growth which is a common observation in calcified atherosclerotic plaques and valves (Kim et al., *Fed Proc*, 35:156–162 (1976)).

Therefore, the calcifying BASMC cultures used in these studies are able to create an extracellular milieu capable of mineralization similar to the mineralization observed in calcified vascular tissues in vivo, supporting their use as a model of ectopic calcification.

EXAMPLE II

Osteopontin Inhibits BASMC Calcification

This example demonstrates that osteopontin inhibits BASMC calcification in vitro, which is a credible model of ectopic calcification in vivo. Therefore, osteopontin will be a therapeutically effective inhibitor of ectopic calcification.

Rat osteopontin was purified from the conditioned medium of rat neonatal smooth muscle cell cultures as described by Liaw et al., supra 74:214–224 (1994), which is incorporated herein by reference. This preparation was judged to be >95% pure based on Coomassie staining and N-terminal sequence analysis.

To examine the effect of osteopontin on BASMC-mediated calcification in vitro, soluble osteopontin or vehicle alone (0.1 mM sodium citrate) was added to the calcifying BASMC cultures. As shown in FIG. 2a, osteopontin at 0.05, 0.5 and 5 μg/ml dose-dependently inhibited calcification assessed at 10 days. For example, 0.5 μg/ml of osteopontin inhibited calcification by approximately 90%, and 5 μg/ml osteopontin almost completely inhibited calcification. In contrast, vehicle alone had no effect (FIG. 2a). Therefore, low concentrations of exogenously applied osteopontin profoundly inhibits extracellular mineralization in a calcifying vascular cell culture system.

To exclude the possibility that contaminants in the osteopontin preparation were responsible for the observed inhibitory effect, immunodepletion experiments were performed. Medium containing 10 μg/ml osteopontin was mixed with 20 mg/ml anti-osteopontin (OP-199) or normal goat IgG, prepared by the method described by Liaw et al., supra (1994) and incubated for 1 hr at room temperature. 250 mg protein-A-sepharose was added and incubated for 1 hr at room temperature. The antibody-protein A sepharose complexes were removed by centrifugation, and the remaining supernatant diluted twenty-fold for use in the calcification studies. Unpaired Student's t test was employed to compare groups and a probability value (p) value less than 0.05 was considered significant.

Medium containing 0.5 μg/ml rat osteopontin inhibited calcification of the cultures by 18 fold (5.05±0.25 μmole/mg for vehicle-treated versus 0.33±0.06 μmole/mg for osteopontin-treated BASMC p=0.0023). Immunodepletion of the osteopontin solution with osteopontin antibody significantly reduced its inhibitory activity (0.33±0.06 μmole/mg for nonimmunodepleted sample versus 2.60±0.43 μmole/mg for anti-osteopontin depleted samples, p=0.0338). In contrast, immunodepletion with normal goat IgG did not affect the inhibitory activity of the rat osteopontin solution (0.49±0.10 μmole/mg for normal goat IgG-treated versus 0.33±0.06 μmole/mg with no immunodepletion, p=0.2480).

These results confirm that the observed inhibition of BASMC-mediated calcification by the osteopontin preparation was specifically due to osteopontin, rather than due to a contaminant.

Figure 2B:
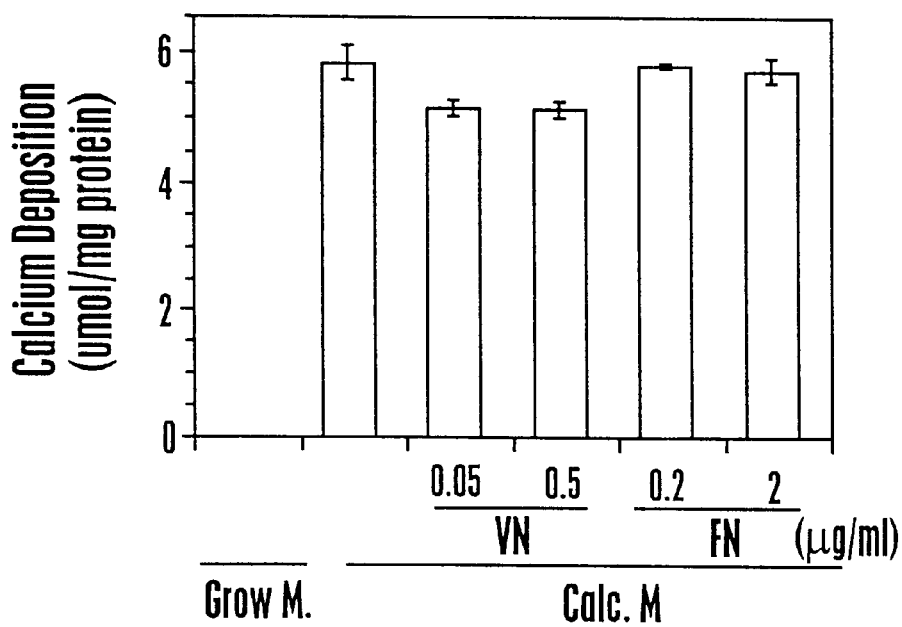

To determine the specificity and uniqueness of osteopontin's effects, two additional noncollagenous extracellular matrix RGD-containing molecules with limited structural and functional homology to osteopontin, vitronectin and fibronectin, were tested for their ability to inhibit BASMC-mediated calcification. Rat plasma vitronectin (Sigma Immunochemicals, USA) and bovine fibronectin (TELIOS Pharmaceutical Inc., USA) were resuspended in PBS at a concentration of 0.5 mg/ml and stored frozen until use. As shown in FIG. 2b, vitronectin (VN) and fibronectin (FN), at equimolar concentrations as were effective for osteopontin, were unable to inhibit calcium deposition. Therefore, the effect of osteopontin on inhibiting vascular calcification is highly specific. Furthermore, these results indicate that the capacity of osteopontin to modulate mineralization are unrelated to its RGD-dependent cell adhesive functions.

Mechanism of Osteopontin Inhibition

The mechanism by which osteopontin inhibited calcification was tested. One possibility was that osteopontin might function in a manner similar to levamisole by affecting alkaline phosphatase activity, thereby inhibiting production of inorganic phosphate from β-glycerophosphate and preventing calcium phosphate deposition.

For cellular alkaline phosphatase activity measurements, cells were cultured in calcification medium in the presence of various concentrations of osteopontin. Cells were washed three times with PBS and cellular proteins were solubilized with 1% Triton X-100 in 0.9% NaCl and centrifuged. Supernatants were assayed for alkaline phosphatase activity by the method described by Bessey et al., *J. Biol. Chem.* 164:321–329 (1946), which is incorporated herein by reference. One unit was defined as the activity producing 1 nmol of p-nitrophenol within 1 minute. Protein concentrations were determined with a BIO-RAD protein assay kit (BIO-RAD). The data were normalized to the protein content of the cell layer.

Figure 3A:
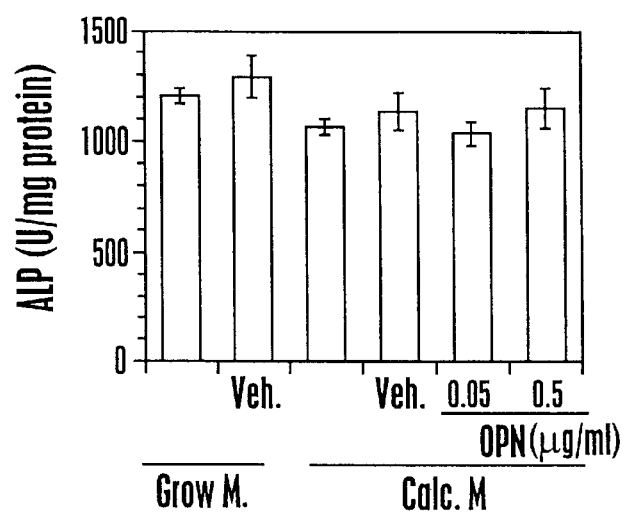
FIG. 3 shows the effects of osteopontin on alkaline phosphatase activity of BASMC (a) and phosphorous concentration in the medium (b) and the effects of levamisole and osteopontin (OPN) on alkaline phosphatase (ALP) activity (c).
Figure 3B:
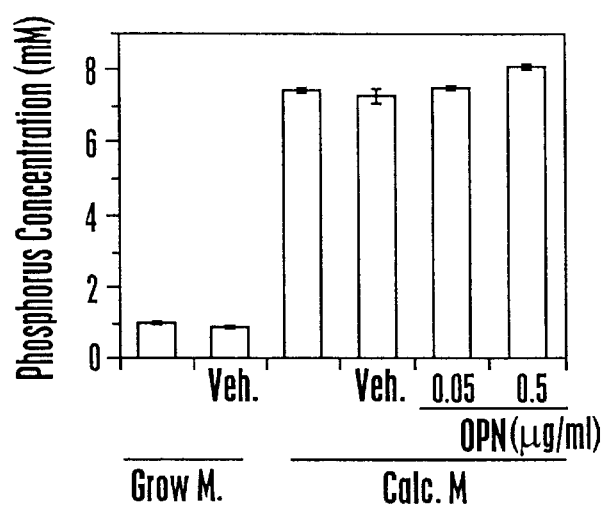
Figure 3C:
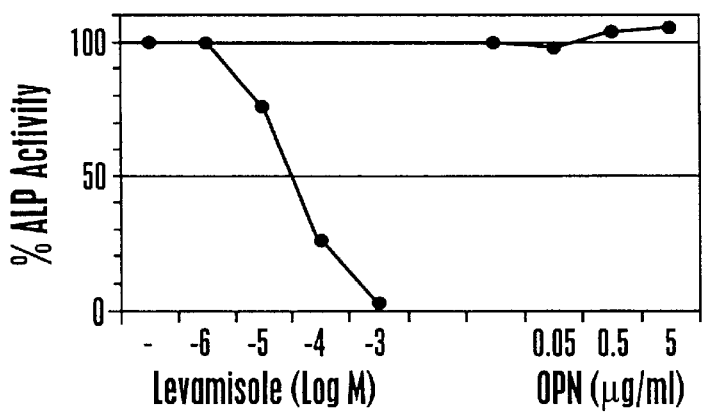

Treatment with osteopontin did not affect the alkaline phosphatase activity of BASMC cultures, as shown in. FIGS. 3a and 3c. The addition of osteopontin also did not reduce the phosphorus concentration of the medium. In contrast, levamisole dose-dependently inhibited BASMC alkaline phosphatase activity (FIG. 3b) and reduced the phosphorus concentration in the culture medium. These results demonstrate that osteopontin does not act by inhibiting alkaline phosphatase activity.

Figure 4A:
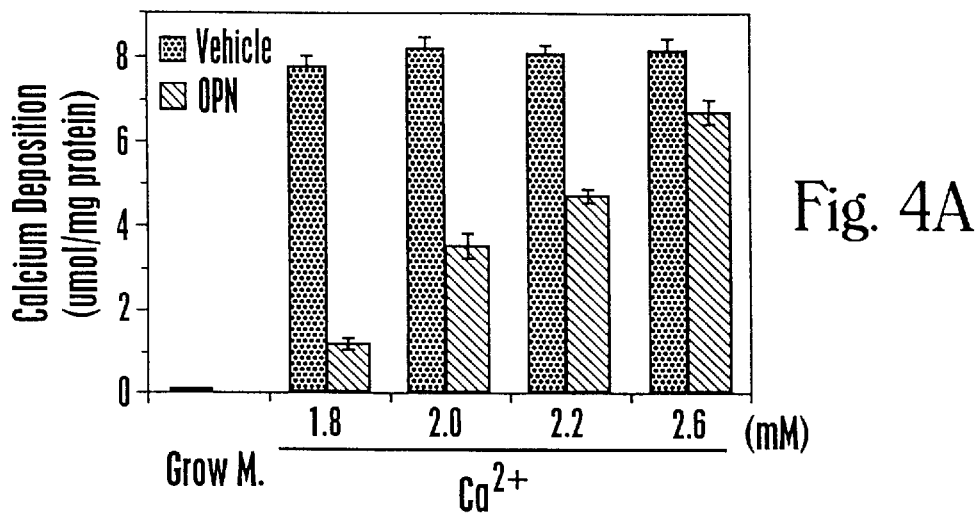
FIG. 4 shows the effects of osteopontin on calcium deposition (a), medium phosphorous concentration (b) and medium calcium concentration (c) at various initial calcium concentrations.
Figure 4B:
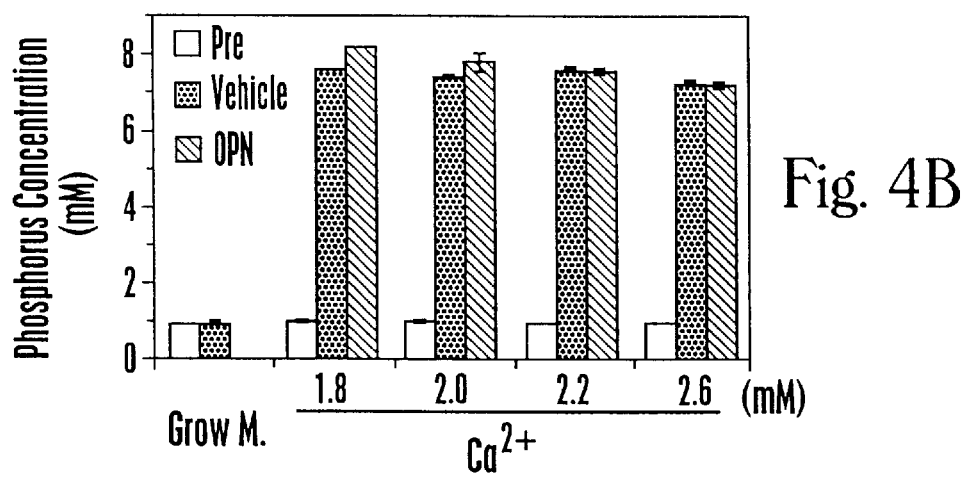

The possibility that osteopontin chelates or sequesters calcium in the culture media to prevent mineralization was also tested. The initial calcification medium was supplemented with increasing concentrations of calcium in the presence of osteopontin or vehicle alone. Cultures were then allowed to calcify in the presence or absence of osteopontin over a 10 day period. As shown in FIG. 4a, increasing the calcium content of the medium was able to overcome the inhibitory effect of osteopontin on calcium deposition, allowing more mineral to be deposited in the cell layer. Consistent with this, a decrease in the phosphorus content (from 8.2 mM to 7.3 mm) of the culture media was noted (FIG. 4b).

Figure 4C:
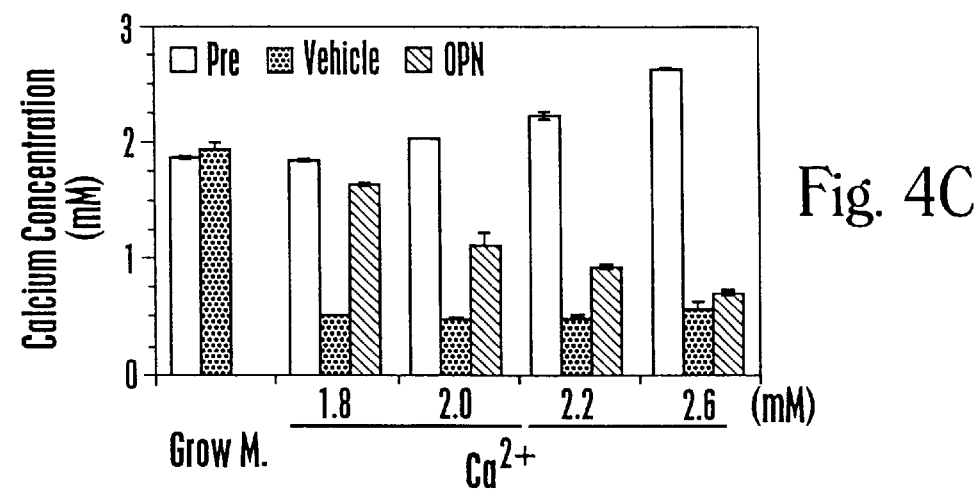

The calcium content of the media at the end of the 10 day period in the presence of osteopontin was also measured. If osteopontin acted by sequestering calcium, it was expected that either a constant or an increasing amount of calcium would be observed in the medium, reflecting retention of calcium in the medium by osteopontin binding. However, the opposite was observed. Calcium concentration in the culture medium was decreased at the end of the 10 day period compared to initial calcium concentrations, and correlated inversely with calcium deposition (compare FIGS. 4a and 4c). Therefore, the inhibitory effect of osteopontin on mineralization is calcium dependent (i.e. decreased by increasing calcium concentrations), but is not attributable to chelation of the calcium available in the medium. This observation is consistent with the known calcium binding properties of osteopontin. It has been shown that about 50 molecules of calcium can be bound by osteopontin at physiological calcium concentrations (Chen et al., *J. Biol. Chem.* 267:24871–24878 (1992)). Hence it would require about 40 $\mu$M osteopontin (2.7 mg/ml) to chelate 2 mM calcium, which is more than 5000 times the amount of osteopontin (0.5 $\mu$g/ml) demonstrated to be effective in inhibiting vascular calcification in the assays described herein.

The ultrastructural localization of endogenous and exogenous osteopontin in the BASMC cultures was also determined using immunogold labeling to further characterize the mechanism of osteopontin inhibition of vascular calcification. BASMC were cultured in calcification media for 7 days to allow mineralization to begin. Purified rat osteopontin (0.5 $\mu$g/ml) was then added until day 10. Cultures were preserved using aldehyde fixative followed by embedding in LR WHITE acrylic resin for immunocytochemistry. Post-embedding immunolabeling was performed using osteopontin antibody (OP-199) and protein A-colloidal gold complex as described by McKee et al., *Microscop. Res. And Tech.,* 33:141–164 (1996), which is incorporated herein by reference. Briefly, thin (80 nm) sections of the cultures were placed on nickel grids and incubated for 5 min with 1% ovalbumin in PBS, followed by incubation with primary antibody for 1 hr, rinsing with PBS, blocking again with ovalbumin, and then exposure to protein A-gold complex for 30 min. After final rinsing with distilled water, grids were air dried and conventionally stained with uranyl acetate and lead citrate and viewed by transmission electron microscopy. The specificity of the OP-199 antibody has been shown previously by Western blotting (Liaw et al., supra, (1994)) and by incubations using pre-immune serum and protein A-gold complex alone.

For these immunogold labeling studies, osteopontin was omitted (vehicle alone) or added on day 7 following initiation of mineralization with $\beta$-glycerophosphate. Under these conditions, exogenously applied osteopontin (0.5 ug/ml) was still able to inhibit BASMC culture calcification by 50% at day 10. A low level of endogenous osteopontin was found in untreated, mineralizing cultures, typically in a diffuse pattern in the mineralized areas. In contrast, in osteopontin-treated cultures, gold particles were abundant at sites of calcification, typically accumulating at the margins of small calcified masses or associating with individual crystal profiles. No gold particles were observed when pre-immune serum and protein A-gold complex alone were used as controls, indicating that a direct interaction of osteopontin with the growing apatite crystals is required for its inhibitory function. Osteopontin was not observed to be associated with unmineralized matrix or cells.

The results described above demonstrate that osteopontin is able to inhibit physiological calcification mediated by vascular cells at low concentrations by direct binding of osteopontin to apatite crystal surfaces and inhibition of crystal growth. Therefore, osteopontin will be therapeutically useful in preventing and treating ectopic calcification.

EXAMPLE III

Calcification of Cultured Human Vascular Cells

This example shows that calcium deposition by cultured human smooth muscle cells in the presence of elevated inorganic phosphate is a credible model of ectopic calcification. Methods for inducing physiologically relevant calcification are described. These methods can be used to assay preparations of osteopontin and fragments thereof for their ability to inhibit ectopic calcification.

The normal adult range of serum inorganic phosphate concentration is about 1.0–1.5 mM. A high serum phosphate level, or hyperphosphatemia, occurs in association with various disease states including, for example, chronic renal failure and subsequent kidney dialysis. In such disease states the serum inorganic phosphate levels can typically exceed 2 mM. In order to model ectopic calcification associated with hyperphosphatemia and to determine the effect of osteopontin and its functional fragments on such calcification, a relevant in vitro model system for calcification was developed, as follows.

Human vascular smooth muscle cells (HSMC) were obtained by enzymatic digestion as described by Ross, *J. Cell Biol.* 50:172–186 (1971) and Liaw et al.,*J. Clin. Invest.* 95:713–724 (1995), incorporated herein by reference. Briefly, medial tissues were separated from segments of human aorta obtained at heart transplant surgery and autopsy, respectively. For plaque SMC, coronary atherectomy-derived tissues were obtained at time of surgery. Small pieces of tissue (1 to 2 mm$^3$) were digested overnight in DMEM supplemented with 165 U/mi collagenase type I, 15 U/ml elastase type III and 0.375 mg/ml soybean trypsin inhibitor at 37° C. Single cell suspensions were placed in 6-well plates and cultured for several weeks in DMEM supplemented with 20% FCS at 37° C. in a humidified atmosphere containing 5% $CO_2$. Cultures that formed colonies were collected at confluence and maintained in growth medium (DMEM containing 15% FBS and 1 MM sodium pyruvate supplemented with 100 U/ml of penicillin and 100 mg/ml of streptomycin; final inorganic phosphate concentration was 1.4 mM). Purity of cultures was assessed by positive immunostaining for alpha-SM actin and calponin and absence of von Willebrand factor staining as described by Ross, supra (1971) and Liaw et al., supra (1995).

Primary human adult and fetal aortic medial and coronary plaque primary cells up to passage 8 were used in these experiments. A fetal and adult HSMC culture was also immortalized using HPV-E6E7 and characterized as described by Perez et al., *Proc. Natl. Acad. Sci. USA* 89:1224–1228 (1992), incorporated herein by reference.

HSMC were routinely subcultured in growth medium. At confluence, cells were switched to calcification medium (DMEM containing 15% FBS and 1 mM sodium pyruvate in the presence of 2 mM inorganic phosphate supplemented with 100 U/ml penicillin and 100 μg/ml of streptomycin) for up to 14 days. The medium was replaced with fresh medium every 2 days. For time-course experiments, the first day of culture in calcification medium was defined as day 0. Calcium deposition was quantified and assessed histochemically and cytochemically as described above in Example I.

In medium containing normal serum phosphate levels (inorganic phosphate, $P_i$, of 1.4 mM), HSMC accumulated very little calcium mineral. In contrast, in the presence of 2 mM inorganic phosphate, calcium deposition increased in a time-dependent manner. For example, on day 9, calcified HSMC vs. uncalcified control was 210.3+/−2.4 vs. 15.1+/−2.4 (μg/mg protein), mean +/− SEM (n+3)). The effect of inorganic phosphate on calcium deposition was dose-dependent over the range of 1.4 mM to 2 mM inorganic phosphate. Induction of calcification by elevated inorganic phosphate appeared to be a general feature of human cells, since primary HSMC derived from different sources (human adult and fetal aortic and coronary plaque) as well as immortalized derivatives of these cells showed similar behavior. No spontaneous deposition of calcium mineral occurred in calcification medium or in medium supplemented with up to 10 mM inorganic phosphate, indicating that cells and/or cell-derived matrix is necessary for mineralization.

To determine whether the observed calcification in the human cell culture system was physiologically relevant, morphological studies were performed. After culturing HSMC in calcification medium for 10 days, granular deposits developed throughout the cell culture. The deposits were identified as phosphate-containing mineral by von Kossa staining, as described in Example I. Black-stained particles were diffusely scattered throughout the cell layer, predominantly in the extracellular regions, with greatest accumulation in multilayered foci. Electron microscopic analysis confirmed the presence of an apatite mineral phase, calcified collagen fibrils and matrix vesicles associated with mineralized cultures, essentially identical to the calcification of bovine SMC cultures in the system described in Example I.

These results demonstrate that HSMC cultures are susceptible to calcification when cultured in media containing inorganic phosphate concentrations typically found in hyperphosphatemic individuals. Furthermore, the observed calcification in the cultured human cells is similar to the ectopic calcification observed in calcified tissues in vivo. Therefore, the HSMC calcification culture system can be used to accurately assess the effect of regulators of ectopic calcification.

EXAMPLE IV

Inhibition of Calcification of Human Vascular Cells By Osteopontin and Functional Fragments Thereof This example demonstrates that osteopontin and exemplary functional fragments of osteopontin effectively inhibit human smooth muscle cell calcification. Therefore, osteopontin can bemused therapeutically to inhibit ectopic calcification.

Osteopontin proteins and functional fragments were assayed for their ability to inhibit ectopic calcification using the HSMC calcification system described in Example III. The osteopontin proteins include full-length human recombinant osteopontin as well as recombinant N-terminal and C-terminal human osteopontin fragments similar to those that would be formed following thrombin cleavage of the native protein, as described by Smith et al., supra (1996). Two N-terminal fragments were used, 10N and 30N, which refer to two differ splice variants of osteopontin. The 30N splice variant contains an additional 14 amino acids, NAVS-SEETNDFKQE (SEQ ID NO:7), which correspond to exon 5 (amino acids 59–72). The 10N fragment contains amino acids 17–58 and 73–160 of native osteopontin, whereas the 30N fragment contains amino acids 17–169. The 10C fragment contains the C-terminal domain of osteopontin, amino acids 170–317.

The N- and C-terminal recombinant osteopontin fragments were-expressed as fusion proteins with GST, purified from bacterial lystates by affinity chromatography on glutathione beads, and cleaved with thrombin. The full-length human recombinant osteopontin was prepared as a His-tagged protein. The size and purity of the resulting recombinant proteins was confirmed by SDS-PAGE analysis (Smith et al., supra (1996)).

Figures 5A, 5B:
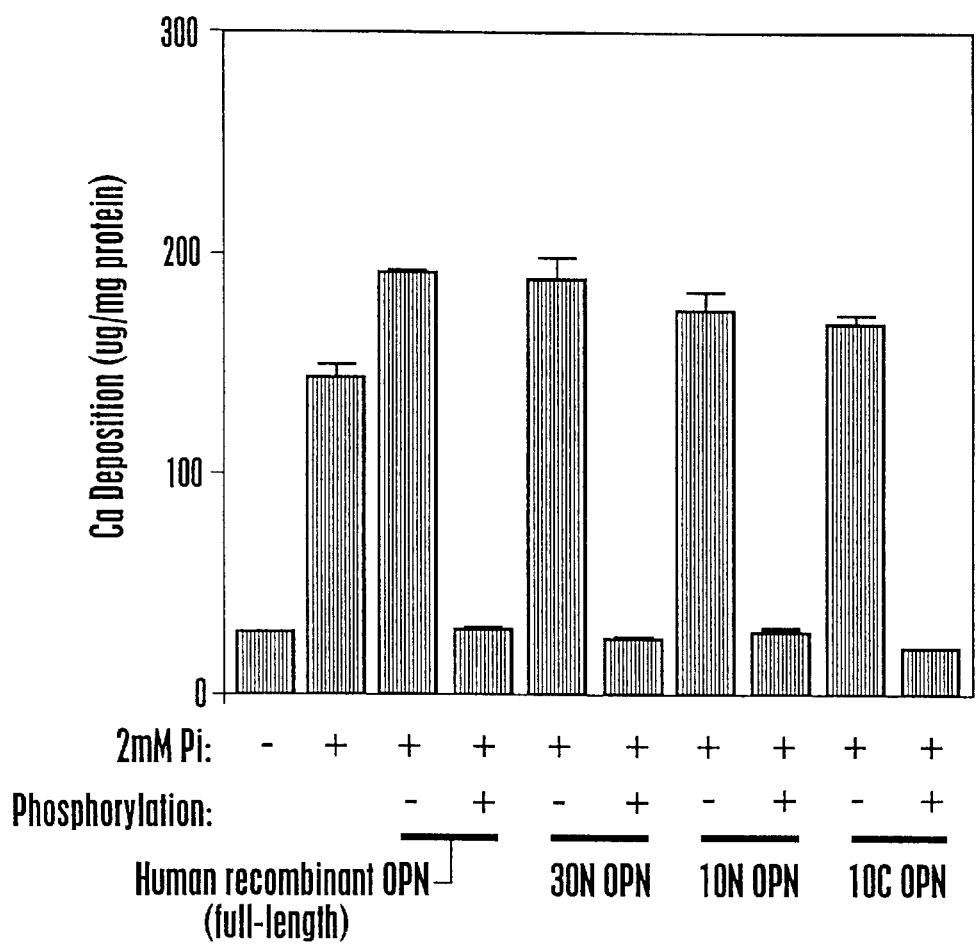
FIG. 5 shows the effects of recombinant osteopontin and its functional fragments on HSMC calcium deposition (a) and the extent of phosphorylation of recombinant osteopontin fragments by casein kinase II (b).

Recombinant osteopontin and its functional fragments were assayed for their ability to inhibit ectopic calcification of human smooth muscle cells (HSMC) either prior to or following phosphorylation by casein kinase II. The amount of phosphate incorporated into osteopontin (OPN) and its fragments achieved by casein kinase II phosphorylation is shown in FIG. 5b. As shown in FIG. 5a, in the presence of high-phosphate calcification medium, calcium deposition into HSMC matrix is reduced to basal levels by the addition of phosphorylated OPN, 30N OPN, 10N OPN or 10C OPN. The non-phosphorylated forms of these proteins do not significantly affect calcium deposition in this assay. These results show that both N- and C-terminal fragments of osteopontin are functional fragments of osteopontin, and that serine-threonine phosphorylation appears to be important for the functional activity of osteopontin and its functional fragments.

Figure 6:
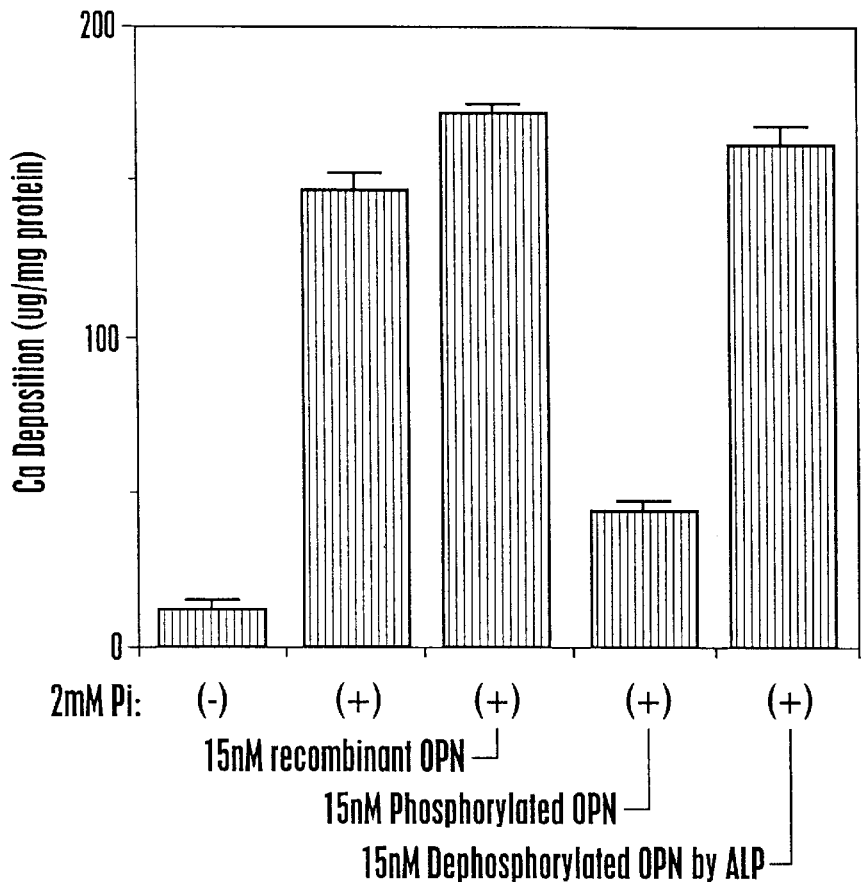
FIG. 6 shows the effect of phosphorylation and dephosphorylation of osteopontin on HSMC calcification.

As shown in FIG. 6, recombinant osteopontin phosphorylated by casein kinase II is able to inhibit HSMC calcification at a concentration of 15 nM. Dephosphorylation with alkaline phosphatase (ALP) reverses this inhibitory ability. These results confirm the importance of phosphorylation for the functional activity of osteopontin and its functional fragments.

Figure 7:
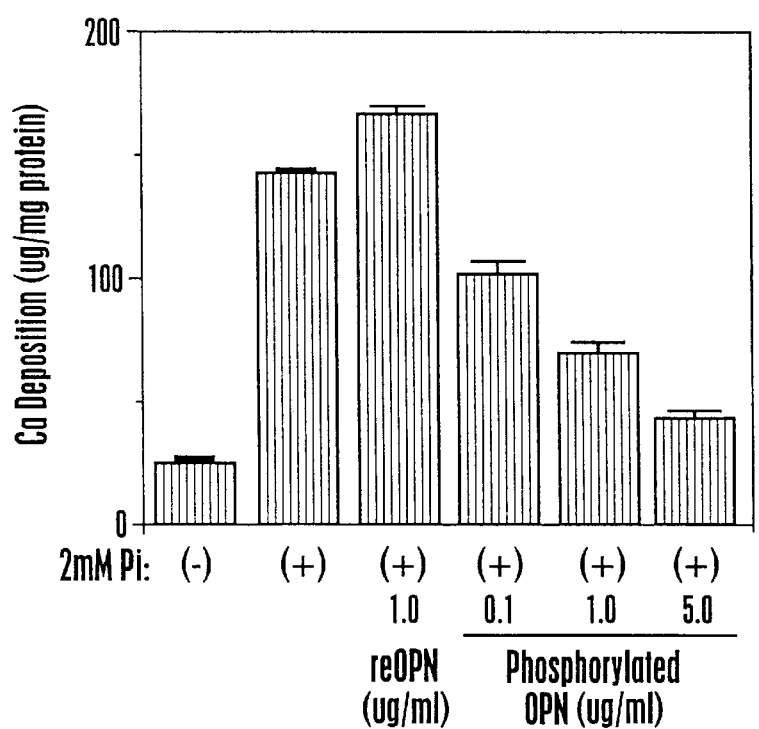
FIG. 7 shows the effect of various concentrations of osteopontin on HSMC calcification.
Figure 8:
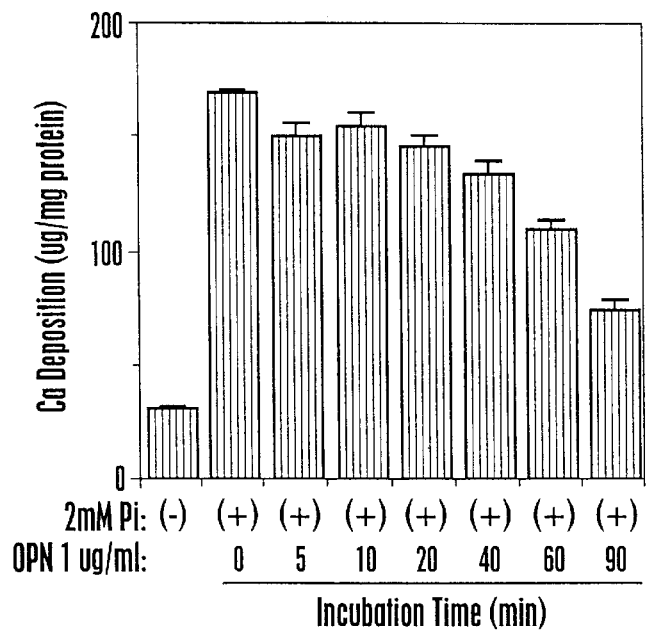
FIG. 8 shows the time course of osteopontin inhibition of HSMC calcification.

The effect of human osteopontin on inhibiting ectopic calcification is dose-dependent over the range of concentrations of 0.1 µg/ml to 5.0 µg/ml (FIG. 7). Furthermore, the effect of osteopontin on inhibiting and reversing ectopic calcification is rapid, with significantly reduced calcium deposition being apparent by 60 minutes, with approximately 50% inhibition observable by 90 minutes following addition (FIG. 8);

These results indicate that osteopontin and exemplary functional fragments thereof are able to effectively inhibit physiologically relevant ectopic calcification of human cells rapidly and at low concentrations. Therefore, full-length osteopontin and functional fragments thereof will be therapeutically effective in inhibiting ectopic calcification in individuals exhibiting or at risk of exhibiting ectopic calcification.

EXAMPLE IV

Osteopontin Inhibits Ectopic Calcification In Vivo

This example shows that osteopontin inhibits ectopic calcification in vivo.

The effect of subcutaneous implantation of porcine prosthetic valves in normal mice and mice deficient in osteopontin was tested to determine the role of osteopontin in ectopic calcification in vivo. Mice deficient in one or both copies of the osteopontin gene are described in Liaw et al., supra (1998). A 5.0 cm³ piece of porcine glutaraldehyde-fixed aortic valve leaflet was subcutaneously implanted into 5–6 week old female mice carrying either the wild type (WT), heterozygote (HTZ) or null allele (KO) for osteopontin. After 14 days, implants were removed, freeze-dried and acid hydrolyzed. Calcium levels were assayed as described in Example I and normalized to the dried weight of the explant.

Figure 9:
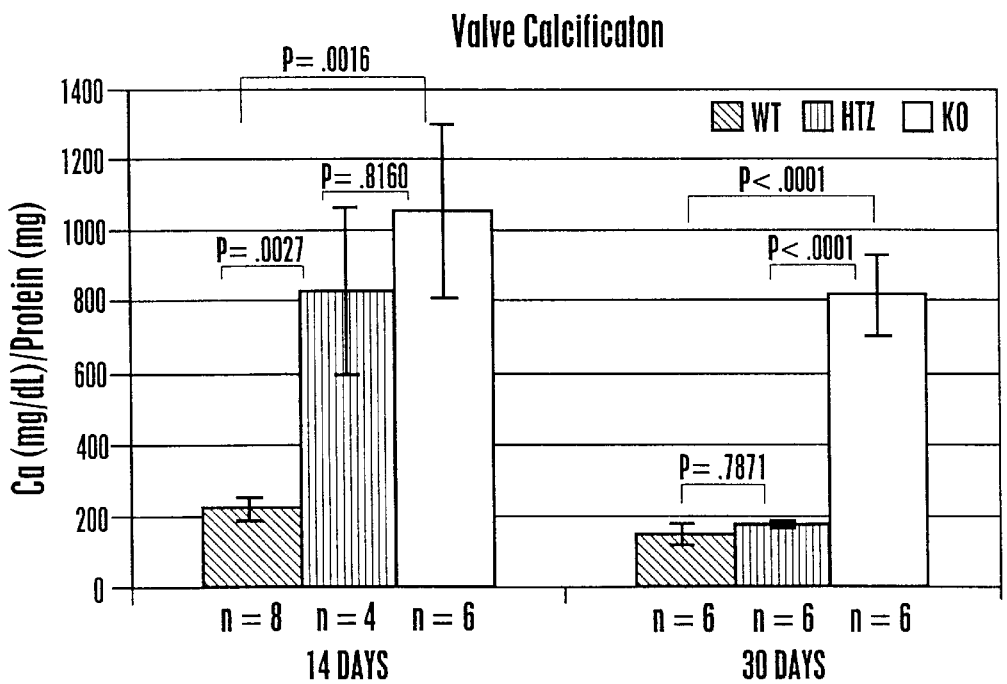
FIG. 9 shows the effect of osteopontin gene copy number on calcification of valves implanted subcutaneously into mice.

As shown in FIG. 9, implanted valves calcify to a significantly greater extent in osteopontin null mice than in wild-type or heterozygous mice. Therefore, consistent with the observed ability of osteopontin to inhibit ectopic calcification in relevant in vitro systems, these results indicate that osteopontin inhibits ectopic calcification in vivo.

The foreign body inflammatory response also appears to be impaired in the osteopontin null mouse. For example, there is an apparent reduction in infiltration by macrophages at the site of valve implantation in the osteopontin null mouse compared to the wild-type or heterozygous mice. Macrophages that normally infiltrate a site of inflammation and ectopic calcification are contemplated to promote removal of calcified deposits by phagocytosis. Therefore, it is contemplated that osteopontin both inhibits hydroxyapatite formation and promotes phagocytotic resorption of calcified deposits by macrophages.

Accordingly, the administration of osteopontin or its functional fragments to an individual will be therapeutically effective in inhibiting ectopic calcification.

Throughout this application various publications have been referenced within parentheses. The disclosure of these publications in their entireties are hereby incorporated by reference in this application in order to more fully describe the state of the art to which this invention applies.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of inhibiting ectopic calcification in an individual, comprising administering to said individual a therapeutically effective amount of osteopontin or a functional fragment thereof sufficient to inhibit ectopic calcification in said individual.

2. The method of claim 1, wherein said ectopic calcification is associated with a condition selected from the group consisting of atherosclerosis, stenosis, restenosis, prosthetic valve replacement, angioplasty, renal failure, tissue injury, diabetes and aging.

3. The method of claim 1, wherein said osteopontin is a polypeptide comprising substantially the amino acid sequence of SEQ ID NO: 2, or a functional fragment thereof.

4. The method of claim 1, wherein said osteopontin or functional fragment thereof is administered with a pharmaceutically acceptable carrier.

5. The method of claim 1, wherein said osteopontin or functional fragment thereof is administered at the site of ectopic calcification.

6. The method of claim 5, wherein said osteopontin or functional fragment thereof contacts a prosthetic device.

7. The method of claim 6, wherein said prosthetic device is a bioprosthetic heart valve.

8. The method of claim 6, wherein said contacting comprises attachment of osteopontin or a functional fragment thereof to said prosthetic device.

* * * * *

UNITED STATES PATENT AND TRADEMARK OFFICE
CERTIFICATE OF CORRECTION

PATENT NO.    : 6,551,990 B2                                     Page 1 of 1
DATED         : April 22, 2003
INVENTOR(S)   : Giachelli et al.

It is certified that error appears in the above-identified patent and that said Letters Patent is hereby corrected as shown below:

Column 1,
Line 5, please delete "numbers HL40079-6A2 and HL18645" and replace with -- number NIH HL18645 --.
Line 6, please delete "EEC9520161" and replace with -- EEC9529161 --.

Signed and Sealed this

Ninth Day of September, 2003

JAMES E. ROGAN
*Director of the United States Patent and Trademark Office*